(12) United States Patent
Zhang et al.

(10) Patent No.: US 11,913,017 B2
(45) Date of Patent: Feb. 27, 2024

(54) EFFICIENT GENETIC SCREENING METHOD

(71) Applicant: The Regents of the University of California, Oakland, CA (US)

(72) Inventors: Kun Zhang, La Jolla, CA (US); Prashant Mali, La Jolla, CA (US); Yan Wu, La Jolla, CA (US); Dongxin Zhao, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1200 days.

(21) Appl. No.: 16/312,907

(22) PCT Filed: Jun. 28, 2017

(86) PCT No.: PCT/US2017/039825
§ 371 (c)(1),
(2) Date: Dec. 21, 2018

(87) PCT Pub. No.: WO2018/005691
PCT Pub. Date: Jan. 4, 2018

(65) Prior Publication Data
US 2019/0330661 A1    Oct. 31, 2019

Related U.S. Application Data

(60) Provisional application No. 62/356,438, filed on Jun. 29, 2016.

(51) Int. Cl.
| | | |
|---|---|---|
| *G16B 25/10* | (2019.01) | |
| *C12N 9/22* | (2006.01) | |
| *C12N 15/10* | (2006.01) | |
| *C12N 15/113* | (2010.01) | |
| *C12N 15/90* | (2006.01) | |
| *G16B 20/20* | (2019.01) | |
| *G16B 40/10* | (2019.01) | |

(52) U.S. Cl.
CPC ............. *C12N 15/907* (2013.01); *C12N 9/22* (2013.01); *C12N 15/102* (2013.01); *C12N 15/113* (2013.01); *G16B 20/20* (2019.02); *G16B 25/10* (2019.02); *G16B 40/10* (2019.02); *C12N 2310/20* (2017.05); *C12N 2320/12* (2013.01); *C12N 2330/31* (2013.01)

(58) Field of Classification Search
None
See application file for complete search history.

(56) References Cited

U.S. PATENT DOCUMENTS

| | | | | |
|---|---|---|---|---|
| 2016/0251648 A1* | 9/2016 | Wang | ............. | C12N 15/63 506/10 |
| 2016/0281111 A1* | 9/2016 | Cotta-Ramusino | ....... | C12N 9/22 |
| 2019/0085324 A1* | 3/2019 | Regev | ............. | G16B 5/00 |

FOREIGN PATENT DOCUMENTS

| | | | | |
|---|---|---|---|---|
| WO | WO 2015/138855 A1 | 9/2015 | | |
| WO | WO 2016/070037 A2 | 5/2016 | | |
| WO | WO-2016070037 A2 * | 5/2016 | ......... | A61K 31/4709 |
| WO | WO 2016/186946 A1 | 11/2016 | | |
| WO | WO-2016186946 A1 * | 11/2016 | ........... | C12N 15/102 |

OTHER PUBLICATIONS

Mali et al., Cas9 as a versatile tool for engineering biology. Nature Methods (2013), 10(10):957-963 (Year: 2013).*
Chain R, Rna Bacteriophage Ms2 Coat Protein Rna Complex, https://www.ncbi.nlm.nih.gov/nuccore/206585733?sat=48&satkey=132759670, [retrieved Jun. 28, 2022]; published 2012 (Year: 2012).*
Zhou et al., High-throughput screening of a CRISPR/Cas9 library for functional genomics in human cells. Nature (2014), 509: 487-491, Online methods and Supplemental material (Year: 2014).*
Heidrich et al., "Investigating CRISPR RNA Biogenesis and Function Using RNA-seq." CRISPR Methods and Protocols. Springer 2015, pp. 1-21 (Year: 2015).*
IUPAC Codes, https://www.bioinformatics.org/sms/iupac.html, [retrieved Dec. 8, 2022] (Year: 2022).*
Jinek et al., A Programmable Dual-RNA-Guided DNA Endonuclease in Adaptive Bacterial Immunity. Science (2012), 337: 816-812 (Year: 2012).*
Wong et al., Multiplexed barcoded CRISPR-Cas9 screening enabled by CombiGEM. PNAS (2016), 113: 2544-2549 (Year: 2016).*
Sheridan et al., A pooled shRNA screen for regulators of primary mammary stem and progenitor cells identifies roles for Asap1 and Prox1. BMC Cancer (2015), 15: 221 (Year: 2015).*
Dugar et al., High-Resolution Transcriptome Maps Reveal Strain-Specific Regulatory Features of Multiple Campylobacter jejuni Isolates. PLOS Genetics (2013), 9(5): 1-15 and Supplemental Methods (Year: 2013).*
Makarova et al., An updated evolutionary classification of CRISPR-Cas systems. Nat Rev Microbiol. (2015), 13(11): 722-736 (Year: 2015).*

(Continued)

*Primary Examiner* — Samuel C Woolwine
*Assistant Examiner* — Catherine Konopka
(74) *Attorney, Agent, or Firm* — Gavrilovich, Dodd & Lindsey LLP

(57) ABSTRACT

A guide RNA comprising: a gRNA spacer sequence at the 5' end of the guide RNA, wherein the spacer sequence is complementary to a target gene, a scaffold sequence that binds to Cas9, and an RNA capture and sequencing domain comprising: a barcode sequence, and a primer binding sequence; nucleic acids and vectors encoding the guide RNA; cells expressing the guide RNA; and a library comprising a plurality of guide RNAs. Also disclosed are methods of introducing a genetic perturbation into a cell, methods of assessing an effect of at least one genetic perturbation on RNA expression in a cell, methods of identifying nucleic acid sequences associated with a disease state and a method of identifying candidate therapeutic agents.

19 Claims, 22 Drawing Sheets

Specification includes a Sequence Listing.

(56) References Cited

OTHER PUBLICATIONS

Miyoshi et al., Structural basis for the recognition of guide RNA and target DNA heteroduplex by Argonaute. Nature Communications (2016), 7:11846, DOI: 10.1038 (Year: 2016).*
Parker and Barford, Argonaute: a scaffold for the function of short regulatory RNAs. Trends in Biochemical Sciences (2006), 31(11): 622-630 (Year: 2006).*
Saayman et al., The therapeutic application of CRISPR/Cas9 technologies for HIV. Expert Opinion on Biological Therapy (2015), 15:6, 819-830 (Year: 2015).*
Kalhor, R. et al. 2017 "Rapidy evolving homing CRISPR barcodes" *Nat Methods* 14(2): 195-200.
Karvelis, T. et al. 2015 "Rapid characterization of CRISPR-Cas9 protospacer adjacent motif sequence elements" *Genome Biology* 16: 253 (in 13 pages).

\* cited by examiner

EFFICIENT GENETIC SCREENING METHOD

STATEMENT REGARDING FEDERALLY SPONSORED R&D

This invention was made with government support under HL123755 awarded by the National Institutes of Health. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. In particular, this application is a U.S. National Phase of International Application No.: PCT/US2017/039825, filed Jun. 28, 2017, designating the U.S. and published in English on Jan. 4, 2018 as WO 2018/005691 A1, which claims the benefit of priority to U.S. Provisional Application Ser. No. 62/356,438, entitled "EFFICIENT GENETIC SCREENING METHOD," filed Jun. 29, 2016, the disclosure of which is hereby incorporated by reference herein in its entirety.

REFERENCE TO SEQUENCE LISTING

The present application is being filed along with a Sequence Listing in electronic format. The Sequence Listing is provided as a file entitled 29626589_1.TXT, created Dec. 21, 2018, which is 12.4 Kb in size. The information in the electronic format of the Sequence Listing is incorporated herein by reference in its entirety.

BACKGROUND OF THE INVENTION

Field of the Invention

Some embodiments relate to guide RNA (gRNA) molecules that contain a spacer sequence complementary to a target gene, a scaffold sequence that binds to Cas9, and an RNA capture and sequencing domain that includes a barcode sequence and a primer binding sequence.

Description of the Related Art

The advent of genome engineering tools, in particular the CRISPR-Cas systems, has allowed rapid and precise modifications of the genome and connecting of these to functional outcomes. Current high-throughput screening approaches have demonstrated their success in annotation of gene dispensability (Wang T, et al. Science. 2014 Jan. 3; 343 (6166):80-4; Shalem 0, et al. Science. 2014 Jan. 3; 343 (6166):84-7; and Wang T, et al. Science. 2015 Nov. 27; 350(6264):1096-101) and perturbation effects. (Dixit A, et al. Cell. 2016 Dec. 15; 167(7):1853-1866.e17; Adamson B, et al. Cell. 2016 Dec. 15; 167(7):1867-1882.e21; and Jaitin D A, et al. Cell. 2016 Dec. 15; 167(7):1883-1896.e15). Despite these achievements, these screens are limited to assaying single-dimensional phenotypes such as cell growth, cell survival, or reporter gene fluorescence.

Researchers typically measure one kind of outcome each time, batch treating and assessing multiple cells. Accordingly, there is a need for improved screening methods.

SUMMARY OF THE INVENTION

Some embodiments relate to a guide RNA comprising: (a) a gRNA spacer sequence at the 5' end of the guide RNA, wherein the spacer sequence is complementary to a target gene, (b) a scaffold sequence that binds to Cas9, and (c) an RNA capture and sequencing domain comprising: (1) a barcode sequence, and (2) a primer binding sequence. In some embodiments, the barcode sequence is uniquely associated with the gRNA spacer sequence. In some embodiments, the barcode sequence is in proximity to a 3' side of the scaffold sequence. In some embodiments, a linker sequence is positioned between the barcode sequence and the primer binding sequence. In some embodiments, the primer binding sequence comprises a polyA sequence. Some embodiments relate to a nucleic acid encoding a guide RNA as disclosed herein. Some embodiments relate to a vector comprising a nucleic acid encoding a guide RNA as disclosed herein. Some embodiments relate to a cell expressing a guide RNA as disclosed herein. In some embodiments, the cell further expresses a Cas9 polypeptide. Some embodiments relate to a library comprising a plurality of guide RNAs as disclosed herein. In some embodiments, the library comprises at least 100 distinct guide RNAs as disclosed herein. In some embodiments, the library comprises at least 1000 distinct guide RNAs as disclosed herein. In some embodiments, the library comprises at least 10000 distinct guide RNAs as disclosed herein. The methods disclosed herein provide a high throughput assay for assessing the impact of even higher numbers of guide RNAs, for example 100,000, 500,000, or 1,000,000 guide RNAs, or a range defined by any two of the preceding values such as 100-1000, 1000-10,000, or 100,000-500,000. In some embodiments, the library is a viral library. In some embodiments, the viral library is a lentiviral library.

Some embodiments relate to a method of introducing a genetic perturbation into a cell comprising: contacting a target nucleic acid in the cell with a guide RNA as disclosed herein, the guide RNA comprising a spacer sequence adapted to introduce the genetic perturbation into the target nucleic acid in a cell; and performing a guide RNA-mediated genetic modification process to introduce the genetic perturbation into the cell. In some embodiments, the guide RNA-mediated genetic modification process comprises a CRISPR genetic modification process. Some embodiments relate to a method of assessing an effect of at least one genetic perturbation on RNA expression in a cell comprising: performing an RNA expression analysis on a cell in which at least one genetic perturbation has been introduced using a guide RNA as disclosed herein, measuring a change in RNA expression of at least one gene, and identifying the at least one genetic perturbation that is responsible for the change in RNA expression of at least one gene by determining the sequence of the barcode in the guide RNA. In some embodiments, the RNA expression analysis comprises a single cell RNA expression analysis. In some embodiments, the at least one genetic perturbation has been introduced by transducing the cell with a virus encoding the guide RNA. In some embodiments, the at least one genetic perturbation introduced by the guide RNA is identified by identifying the barcode in the guide RNA. In some embodiments, the barcode is identified by extending a primer which hybridizes to a 3' region of the guide RNA. In some embodiments, the primer hybridizes to a polyA sequence in the 3' region of the guide RNA. In some embodiments, the method comprises capturing the guide RNA and RNAs of the transcriptome expressed in the cell using oligo-d(T) capture probes, wherein detection of the at least one genetic perturbation is linked to detection of the change in RNA expression of the at least one gene in the transcriptome of the cell. In some embodiments, the at least one effect is assessed by performing a single cell RNA expression analysis. In some embodiments, the effects of at least 100 different genetic perturbations are assessed. In some embodiments, the effects of at least 1,000 different genetic perturbations are assessed. In some embodiments, the effects of at least 10,000 different genetic perturbations are assessed. In some embodiments, the at least one genetic perturbation is selected from the group consisting of an insertion, a deletion and a point mutation. In some embodiments, the at least one genetic perturbation is selected from the group consisting of a genetic perturbation which eliminates expression of a target gene, a genetic perturbation which increases expression of a target gene, and a genetic perturbation which decreases expression of a target gene. Some embodiments further comprise determining the effects of the at least one genetic perturbation on cell differentiation. In some embodiments, the number of genetic pertubations is 2 or more, such as 3, 4, 5, 6, 7, 8, 9, 10 or a range defined by any two of the preceding values, such as 2-4, 3-6 or 2-5. In some embodiments, the cell differentiation is differentiation of an induced pluripotent stem cell. In some embodiments, the induced pluripotent stem cell is an induced pluripotent stem cell which has differentiated into a teratoma. In some embodiments, the at least one genetic perturbation is introduced in a nucleic acid sequence selected from the group consisting of a nucleic acid sequence encoding a polypeptide product, a nucleic acid sequence encoding an RNA product, a nucleic acid sequence which effects a level of gene expression, and a non-coding nucleic acid sequence. In some embodiments, the at least one genetic perturbation is selected from the group consisting of a perturbation which disrupts a SNP, a perturbation which disrupts a promoter or enhancer, and a perturbation which deletes a promoter or enhancer. Some embodiments further comprise assessing the effects of the at least one genetic perturbation on at least one physiological phenotype of the cell. Some embodiments further comprise enhancing the efficiency of the guide RNA mediated genetic modification process. In some embodiments, the efficiency of the guide RNA mediated genetic modification process is enhanced using Trex2. Some embodiments further comprise: using a bioinformatics tool to call the guide RNA(s) and corresponding RNA expression profiles present in each cell sequenced, and performing computational analysis to detect changes in RNA expression due to specific gene knockouts. In some embodiments, the computational analysis comprises clustering and/or outlier detection. Some embodiments relate to a method of identifying nucleic acid sequences associated with a disease state comprising; assessing the effects of at least one genetic perturbation using a method disclosed herein; and identifying one or more genetic perturbations which produce effects on RNA expression similar to the disease state.

Some embodiments relate to a method of identifying candidate therapeutic agents comprising: assessing the effects of at least one genetic perturbation using a method of disclosed herein; identifying one or more genetic perturbations which produce effects on RNA expression similar to the disease state; and screening a plurality of candidate therapeutic agents to identify candidate therapeutic agents which act on at least one product encoded by a gene in or near which the at least one genetic perturbation which produced effects on RNA expression similar to the disease state is located. In some embodiments, the candidate therapeutic agent is selected from the group consisting of a naturally occurring agent and a synthetic agent. In some embodiments, the naturally occurring agent is selected from the group consisting of a naturally occurring chemical compound and a naturally occurring biological molecule. In some embodiments, the biological molecule comprises an antibody. Some embodiments relate to a method of assessing the effects of at least one genetic perturbation on a cell comprising evaluating at least one phenotype in a cell in which the at least one genetic perturbation has been introduced using a guide RNA as disclosed herein. In some embodiments, the at least one phenotype is a phenotype in at least one germ layer of a teratoma. In some embodiments, the teratoma is generated through differentiation of an induced pluripotent stem cell.

Some embodiments are described in the following numbered paragraphs:

1. A guide RNA comprising a comprising a barcode sequence
2. The guide RNA of Paragraph 1, wherein said barcode sequence is uniquely associated with a spacer sequence.
3. The guide RNA of any one of Paragraphs 1 and 2, wherein said barcode sequence is in proximity to a 3' side of a scaffold sequence.
4. The guide RNA of any one of Paragraphs 1-3, wherein a linker sequence is positioned between said barcode sequence and a primer binding sequence.
5. The guide RNA of Paragraph 4, wherein said primer binding sequence comprises a polyA sequence.
6. A nucleic acid encoding the guide RNA of any one of Paragraphs 1-5.
7. A cell expressing the guide RNA of any one of Paragraphs 1-5.
8. The cell of Paragraph 7, wherein said cell further expresses a Cas9 polypeptide.
9. A library comprising a plurality of guide RNAs of any one of Paragraphs 1-5.
10. The library of Paragraph 9, wherein said library comprises at least 100 distinct guide RNAs of any one of Paragraphs 1-5.
11. The library of Paragraph 9, wherein said library comprises at least 1000 distinct guide RNAs of any one of Paragraphs 1-5.
12. The library of Paragraph 9, wherein said library comprises at least 10000 distinct guide RNAs of any one of Paragraphs 1-5.
13. The library of any one of Paragraphs 9-12 wherein said library is a viral library.
14. The library of Paragraph 13, wherein said viral library is a lentiviral library.
15. A method of introducing a genetic perturbation into a cell comprising:
   contacting a target nucleic acid in said cell with a guide RNA of any one of Paragraphs 1-5 said guide RNA comprising a spacer sequence adapted to introduce said genetic perturbation into said target nucleic acid in a cell; and
   performing a guide RNA-mediated genetic modification process to introduce said genetic perturbation into said cell.
16. The method of Paragraph 15, wherein said guide RNA-mediated genetic modification process comprises a CRISPR genetic modification process.
17. A method of assessing the effects of at least one genetic perturbation on RNA expression in a cell comprising performing an RNA expression analysis on a cell in which said at least one genetic perturbation has been introduced using a guide RNA of any one of Paragraphs 1-5.
18. The method of Paragraph 17, wherein said RNA expression analysis comprises a single cell RNA expression analysis.

19. The method of any one of Paragraphs 17 and 18, wherein said at least one genetic perturbation has been introduced by transducing said cell with a virus encoding said guide RNA.

20. The method of any one of Paragraphs 17-19, further comprising identifying the at least one genetic perturbation introduced by said guide RNA.

21. The method of Paragraph 20, wherein the at least one genetic perturbation introduced by said guide RNA is identified by identifying the barcode in said guide RNA.

22. The method of Paragraph 21, wherein said barcode is identified by extending a primer which hybridizes to a 3'region of said guide RNA.

23. The method of Paragraph 22, wherein said primer hybridizes to a polyA sequence in said 3' region of said guide RNA.

24. The method of any one of Paragraphs 17-23, wherein the effects of at least 100 different genetic perturbations are assessed.

25. The method of any one of Paragraphs 17-23, wherein the effects of at least 1,000 different genetic perturbations are assessed.

26. The method of any one of Paragraphs 17-23, wherein the effects of at least 10,000 different genetic perturbations are assessed.

27. The method of any one of Paragraphs 17-23, wherein said at least one genetic perturbation is selected from the group consisting of an insertion, a deletion and a point mutation.

28. The method of any one of Paragraphs 17-27, wherein said at least one genetic perturbation is selected from the group consisting of a genetic perturbation which eliminates expression of a target gene, a genetic perturbation which increases expression of a target gene, and a genetic perturbation which decreases expression of a target gene.

29. The method of any one of Paragraphs 17-28, further comprising determining the effects of said at least one genetic perturbation on cell differentiation.

30. The method of Paragraph 29, wherein said cell differentiation is differentiation of an induced pluripotent stem cell.

31. The method of Paragraph 30, wherein said induced pluripotent stem cell is an induced pluripotent stem cell which has differentiated into a teratoma.

32. The method of any one of Paragraphs 17-31, wherein said at least one genetic perturbation is introduced in a nucleic acid sequence selected from the group consisting of a nucleic acid sequence encoding a polypeptide product, a nucleic acid sequence encoding an RNA product, a nucleic acid sequence which effects a level of gene expression, and a non-coding nucleic acid sequence.

33. The method of any one of Paragraphs 17-32, wherein said at least one genetic perturbation is selected from the group consisting of a perturbation which disrupts a SNP, a perturbation which disrupts a promoter or enhancer, and a perturbation which deletes a promoter or enhancer.

34. The method of any one of Paragraphs 17-33, further comprising assessing the effects of said at least one genetic perturbation on at least one physiological phenotype of said cell.

35. The method of any one of Paragraphs 17-34, further comprising enhancing the efficiency of said guide RNA mediated genetic modification process.

36. The method of Paragraph 35, wherein the efficiency of said guide RNA mediated genetic modification process is enhanced using Trex2.

37. A method of identifying nucleic acid sequences associated with a disease state comprising;
assessing the effects of at least one genetic perturbation using the method of any one of Paragraphs 17-36; and
identifying one or more genetic perturbations which produce effects on RNA expression similar to said disease state.

38. A method of identifying candidate therapeutic agents comprising:
assessing the effects of at least one genetic perturbation using the method of any one of Paragraphs 17-36;
identifying one or more genetic perturbations which produce effects on RNA expression similar to said disease state; and
screening a plurality of candidate therapeutic agents to identify candidate therapeutic agents which act on at least one product encoded by a gene in or near which said at least one genetic perturbation which produced effects on RNA expression similar to said disease state is located.

39. The method of Paragraph 38, wherein said candidate therapeutic agent is selected from the group consisting of a naturally occurring agent and a synthetic agent.

40. The method of Paragraph 39, wherein said naturally occurring agent is selected from the group consisting of a naturally occurring chemical compound and a naturally occurring biological molecule.

41. The method of Paragraph 40, wherein said biological molecule comprises an antibody.

42. A method of assessing the effects of at least one genetic perturbation on a cell comprising evaluating at least one phenotype in a cell in which said at least one genetic perturbation has been introduced using a guide RNA of any one of Paragraphs 1-5.

43. The method of Paragraph 42, wherein said at least one phenotype is a phenotype in at least one germ layer of a teratoma.

44. The method of Paragraph 43, wherein said teratoma is generated through differentiation of an induced pluripotent stem cell.

45. A nucleic acid adapted to affect gene expression, said nucleic acid comprising a comprising a barcode sequence.

46. The nucleic acid of Paragraph 45, wherein said nucleic acid is selected from the group consisting of a nucleic acid comprising an open reading frame encoding a polypeptide and a nucleic acid encoding an interfering RNA.

47. The nucleic acid of any one of Paragraphs 45 and 46, further comprising a primer binding sequence.

48. The nucleic acid of Paragraph 47, wherein said primer binding sequence is positioned such that a primer binding to said primer binding sequence can be extended to determine the sequence of said barcode.

49. The nucleic acid of any one of Paragraphs 47 and 48, wherein said primer binding sequence comprises a polyA sequence.

50. A vector comprising the nucleic acid of any one of Paragraphs 45-49.

51. A cell expressing the nucleic acid of any one of Paragraphs 45-49.

52. library comprising a plurality of nucleic acids any one of Paragraphs 45-49.

53. The library of Paragraph 52, wherein said library comprises at least 100 distinct nucleic acids of any one of Paragraphs 45-49.

54. The library of Paragraph 52, wherein said library comprises at least 1000 nucleic acids of any one of Paragraphs 45-49.

55. The library of Paragraph 52, wherein said library comprises at least 10000 nucleic acids of any one of Paragraphs 45-49.

56. The library of any one of Paragraphs 52-55 wherein said library is a viral library.

57. The library of Paragraph 56, wherein said viral library is a lentiviral library.

58. The library of any one of Paragraphs 52-57, wherein said library is an ORFeome library or an RNAi library.

59. A method of evaluating the effects of an alteration of gene expression comprising:
   introducing a nucleic acid of any one of Paragraphs 45-49. into a cell;
   determining at least one effect resulting from the introduction of said nucleic acid; and
   identifying the gene whose altered expression is responsible for said at least one effect by determining the sequence of said barcode in said nucleic acid.

60. The method of Paragraph 59, wherein the effects of altering the expression of at least 100 different genes are assessed.

61. The method of Paragraph 59, wherein the effects of altering the expression of at least 1000 different genes are assessed.

62. The method of Paragraph 59, wherein the effects of altering the expression of at least 10000 different genes are assessed.

63. The method of any one of Paragraphs 59-62, wherein said at least one effect is assessed by performing a single cell RNA expression analysis.

DETAILED DESCRIPTION

Figure 1:
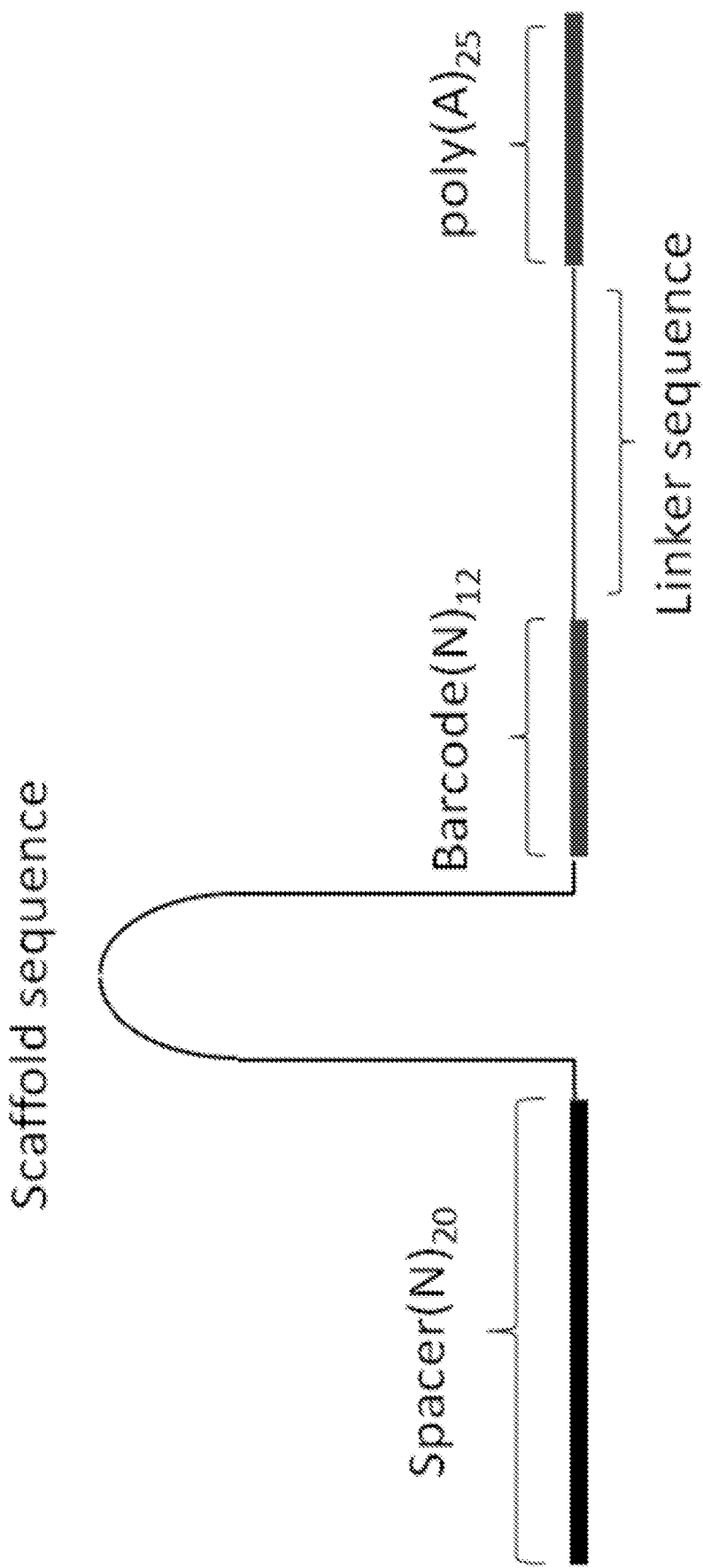
FIG. 1 illustrates a custom CRISPR guide RNA design.

Some embodiments relate to a method for highly efficient characterization of the functional consequences of genetic modifications in many single mammalian cells in parallel. Some embodiments utilize a CRISPR system designed such that the exact genetic modification in each cell as well as the functional consequences of the modification in the form of gene expression, can be determined in a massively parallel manner. In some embodiments, the methods and compositions described herein may be utilized to provide comprehensive characterization of disease-causing genetic mutations, massive screening of potent T-cells for immunotherapy, high-throughput bio-production optimization, and discovering therapeutically relevant neutralizing antibodies.

Some embodiments relate to a CRISPR guide RNA design, which allows for the first time genetic perturbations to be connected with the profile of all genes in a cell. This allows examination of a variety of different outcomes in one shot, many of which are not possible to quantify with the existing approaches. Being able to assess the functional outcomes on a larger number of individual cells also greatly improves the efficiency of the screen by orders of magnitude. Thus, some embodiments greatly expand what is possible in terms of screening and also dramatically improves efficiency.

Some embodiments provide a method for highly efficient characterization of the functional consequences of genetic modifications in many single mammalian cells in parallel. Some embodiments employ a CRISPR system designed such that the exact genetic modification in each cell as well as the functional consequences of the modification in the form of gene expression, can be determined in a massively parallel manner. Some embodiments may be utilized to allow comprehensive characterization of disease causing genetic mutations, massive screening of potent T-cells for immunotherapy, high-throughput bio-production optimization, and discovery of therapeutically relevant neutralizing antibodies.

Some embodiments relate to a CRISPR guide RNA construct that includes a poly(A) sequence connected to a DNA barcode, constituting an RNA capture and sequencing domain. The barcode sequence may be completely arbitrary. In some instances, a pattern in the barcode sequence may be chosen so that there is an underlying pattern to the barcode so that mutations, such as during sequencing, can be computationally resolved to ensure accurate barcode calling. The barcode sequence is of a defined length, non-limiting examples including 7, 8, 9, 10, 11, 12, 13, 14, 15, 16, 17 18, 19, 20 or more nucleotides in length, or a range defined by any two of the preceding values. Each DNA barcode can be matched to a unique genetic modification, whereas the poly(A) sequence enables one to simultaneously read out the quantitative information of either the full transcriptome or a select subset of genes, as well as the identity of genetic perturbations in single cells of a heterogeneous population.

Most high throughput genetic screening technology relies on phenotypes that can be coupled to some sort of easily detectable phenotypes, such as fluorescent cell sorting, cell imaging, or cell death. However, many genetic variants or perturbations may result in a phenotype that is much more subtle and cannot be easily detected by existing screening technologies. Some embodiments provided herein enable detection of these subtle phenotypes by assaying changes in gene expression that result when a genetic perturbation is made. This not only provides a much richer phenotype (the expression levels of more than 20 k genes), it allows interrogation of gene pathways and regulatory networks in a novel fashion. The effect of a genetic perturbation on all genes may be directly read out, combining this data with existing knowledge of gene regulatory pathways to further our understanding of how genes interact.

Additionally, some embodiments retain the scalability of previous high throughput genetic perturbation screening technology since the screen is conducted in a "pooled format".

Shalem et al and Wang et al illustrate pooled CRISPR knockout screens for cell death (Shalem et al. 2014 Science, 343(6166): 84-87) (Wang et al. 2014 Science, 343(6166): 80-84). Additionally, there are examples of CRISPR-Cas9 knockout screens for imageable phenotypes such as protein expression via immunostaining (Parnas et al. 2015 Cell, 162(3): 675-686). Recently, there have been CRISPR-Cas9 screens that result in overexpression or repression of the target genes (instead of a gene knockout) (Konermann et al. 2015 Nature, 517(7536): 583-588). Some embodiments provided herein can be easily modified to use gene activation/repression instead of gene knockouts.

An embodiment of an exemplary custom CRISPR guide RNA construct illustrated in FIG. 1. A poly(A) sequence is added so that the guide RNA can be detected with traditional single cell RNAseq technologies that use poly(T) primers. Since many single cell RNA-seq technologies only sequence the 3' end of the RNA, in some embodiments, a barcode may be included near the poly(A) tail that can be used to identify the spacer sequence (which itself will most likely not be sequenced). Each barcode should map uniquely to a spacer sequence.

Figure 2:
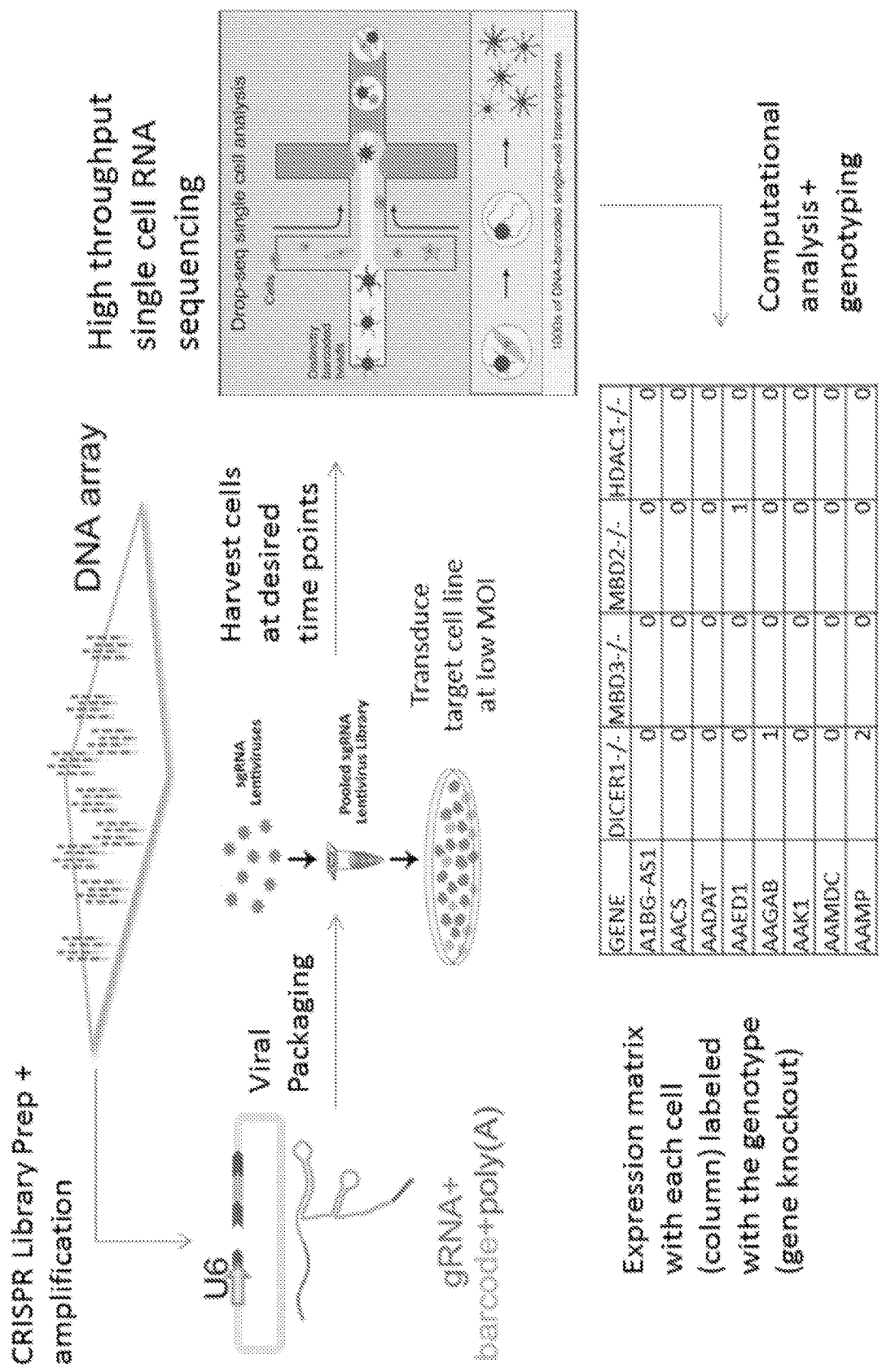
FIG. 2 illustrates one embodiment of a high throughput screening approach.

An embodiment of an exemplary high throughput screening approach is illustrated in FIG. 2. Custom gRNA oligos are ordered on a DNA array, a library is constructed and amplified, and the barcode+poly(A) tail are added to the gRNA. The CRISPR knockout library is packaged in viral vectors and the target cell line is transduced, adjusting the multiplicity of infection (MOI) to the desired levels. Afterwards, the cells are harvested and single cell RNA sequencing is performed. In some embodiments, single cell RNA sequencing is performed using Drop-Seq (Macosko et al. 2015 Cell, 161(5): 1202-1214), but it will be appreciated that the custom gRNA construct and screening approach provided herein is compatible with any single cell RNA-sequencing technology that uses poly(T) primers. After sequencing, a custom bioinformatics pipeline may be used to call the guide RNA(s) present in each cell sequenced and thus obtain the genes that were knocked out in these cells. With the gene knockouts and the RNA expression profile, computational analysis such as clustering, and outlier detection may be performed to detect changes in RNA expression due to specific gene knockouts.

Figure 3:
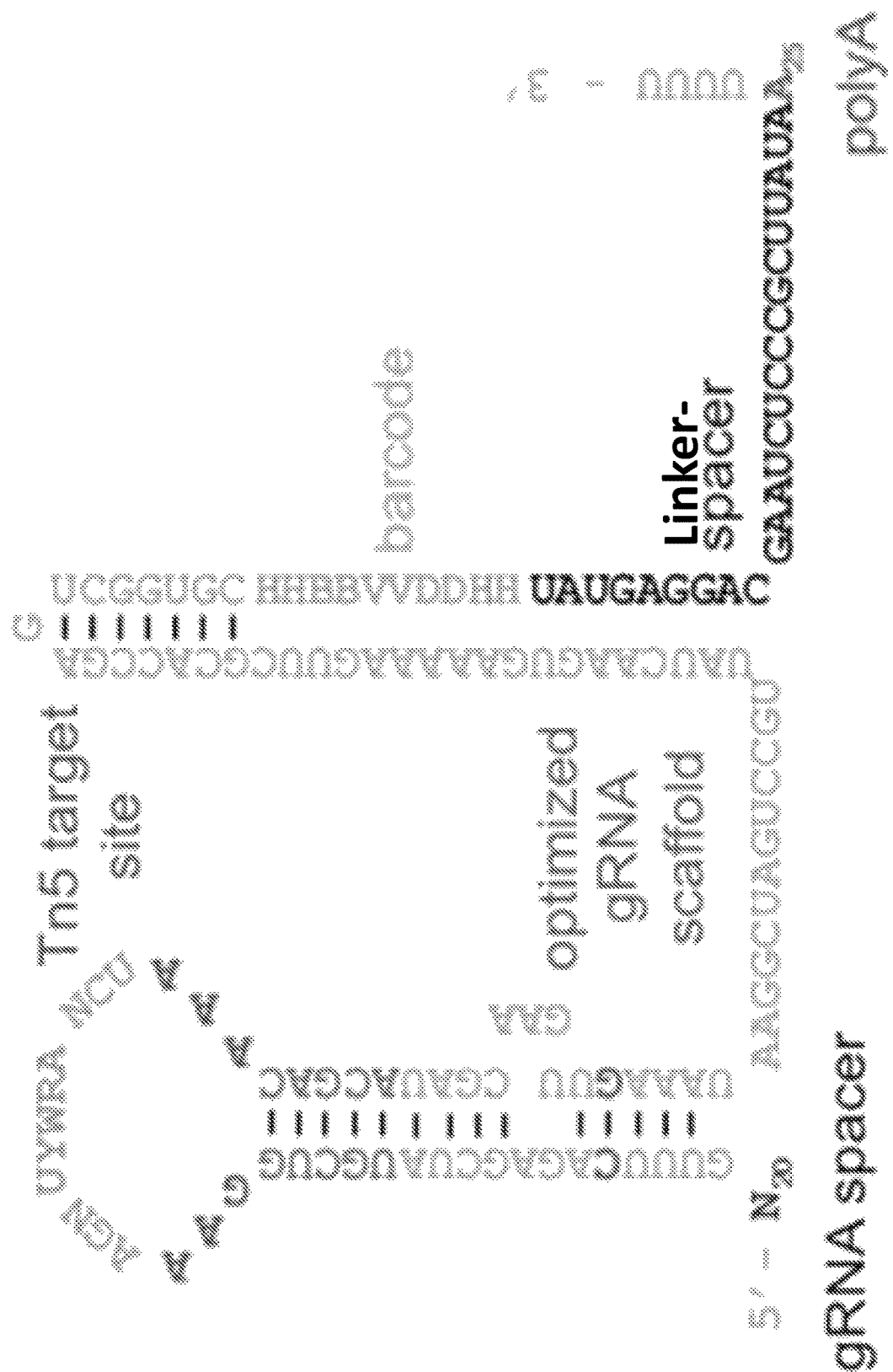
FIG. 3 illustrates an exemplary CRISPR-Cas9 construct. The nucleotide sequence shown corresponds to SEQ ID NO: 1. The barcode sequence may be completely arbitrary. In some instances, a pattern in the barcode sequence may be chosen so that there is an underlying pattern to the barcode. For example, the barcode shown (HHBBVVDDHH) may have any nucleotide present at each position or there may be an underlying pattern contained within the barcode.
Figure 4:
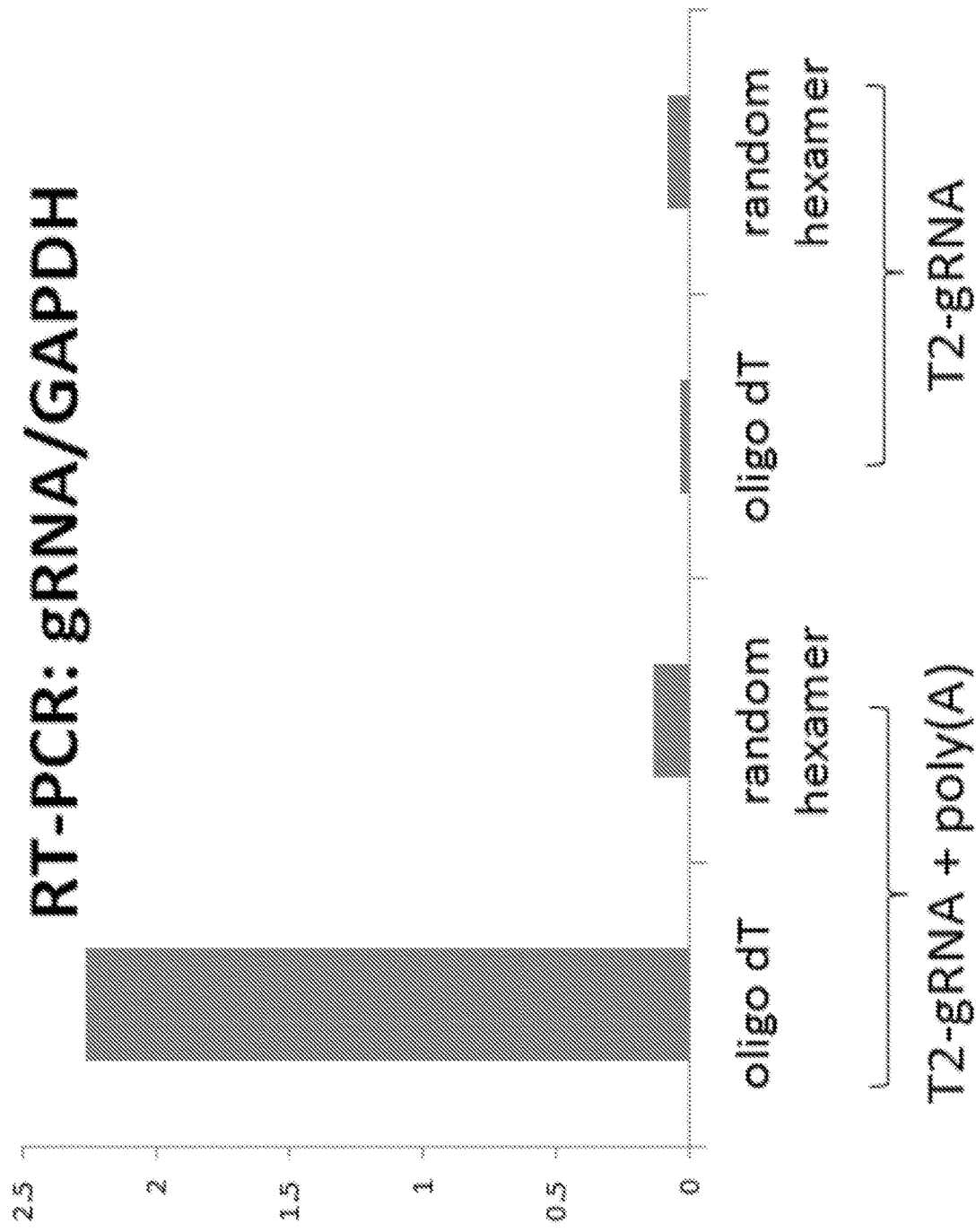
FIG. 4 shows that an exemplary gRNA construct can be detected via qPCR with poly(T) primers as shown in FIG. 4, and that the same gRNA without the polyA tail cannot be detected via qPCR.

In some embodiments, the CRISPR-Cas9 construct shown in FIG. 3 may be used. This gRNA construct can be detected via qPCR with poly(T) primers as shown in FIG. 4, while the same gRNA without the polyA tail cannot be detected via qPCR. Furthermore, this gRNA construct can be detected via single cell RNA-seq, such as Drop-Seq. Approximately 25% of single cells sequenced have a clearly identifiable single gRNA expressed. DropSeq implementation has been validated by verifying that our doublet rate is less than 5% via a species mixing experiment where we mixed human and mouse cells. Thus, more than 95% of the cells are true single cells.

In some embodiments, in the optimized gRNA design provided herein, one can incorporate polyAs in the regions highlighted by underlined N's:

(SEQ ID NO: 5)
GN<u>NNNNNNNNNNNNNNNNNNNNN</u>GTTTgAGAGCTAgg<u>NNNNNNNNNN</u>

<u>NNNNNNNNNN</u>ccTAGCAAGTTcAAATAAGGCTAGTCCGTTcTCAACT

Tggcca<u>NNNNNNNNNNNNNNNNNNNNNNN</u>ctgcagggccAAGTGGCACCGAGT

CGGTGC<u>NNNNNNNNNNNNNNNNNNNNN</u>TTTTTT

In some embodiments, the compositions and methods provided herein may be used to characterize the functions of >1000 genes (or genetic loci) across a variety of cell types.

In some embodiments, the methods and compositions provided herein may be used to identify potential disease causing genetic perturbations. While Genome Wide Association Studies and private companies such as 23AndMe have identified some genetic variants associated with diseases, the phenotypic effects of most genetic variants is still unknown. The methods and compositions provided herein may be used for identifying the effects of these variants.

In some embodiments, the methods and compositions provided herein may be used to identify promising therapeutic targets. Target identification can be a difficult process since it can be difficult to discern the effects of inhibiting a specific protein in a high throughput manner. The screening methods provided herein may be used to detect any effect a gene knockout may have on a transcriptome, allowing for rapid target identification in any number of disease specific cell lines.

In some embodiments, the methods and compostions provided herein may be used for optimizing biomolecule production in eukaryotic cells. Chinese Hamster Ovary (CHO) cells are widely used to produce recombinant mammalian proteins (Kim et al. 2012). The methods and compositions provided herein can be used to optimize protein production by determining which genetic perturbations maximize RNA expression of the recombinant protein.

Additionally, the methods and compositions described herein can be easily ported to prokaryotic cell lines such as *E. Coli*.

In some embodiments, the methods and compositions provided herein may be used for discovering therapeutically relevant neutralizing antibodies.

With the rapid advances in DNA sequencing, we now have a near-complete human genome, a fairly comprehensive catalog of germline and somatic variants, as well as rich annotations of functional genomic elements. The next challenge in the field is to obtain a complete functional annotation of genetic variants and genomic elements at the cellular and organismal levels.

Genome editing technology, in particularly the CRISPR/Cas9 system, has allowed rapid and precise modifications of the genome and connecting of these to functional outcomes. However, current high-throughput screening approaches rely on phenotypes that can be coupled to cell survival, cell imaging, fluorescent cell sorting, or affinity enrichments. Genetic variants that have more subtle phenotypic consequences, which might represent the majority, are not amenable to such screens. Furthermore, screening of natural genetic variation via assaying of individual cell lines under in vitro culture conditions also has limited throughput and might miss functional differences that depend on specific physiological contexts.

Some embodiments described herein provide a next-generation functional genetic screening method that can overcome these fundamental limitations. Specifically, by treating the full transcriptome of a single cell as the phenotype, any genetic perturbation that leads to systematic transcriptional changes, including many "un-screenable traits", become detectable. To scale this, in some embodiments, a CRISPR/Cas9 design is provided whereby genetic modifications in large numbers of individual cells can be linked via unique RNA barcodes to the transcriptome of the same cells. This allows aggressive multiplexing not only on the number of genetic changes but also different cell types in pooling experiments. The scalability is only limited by sequencing power. This method greatly accelerates the functional annotation of genetic variants, including many variants of unknown significance, across various normal and diseased cell types and tissues.

Some embodiments provide en masse single-cell phenotyping and functional screening of coding changes. In some embodiments, a CRISPR/Cas9 system that is compatible with massively parallel single-cell transcriptome sequencing using droplets may be used. Some embodiments enable characterization of the transcriptional states of at least 50,000 single cells and connection of them with 5,000 genetic modifications per single experiment. In some embodiments, the methods and compositions provided herein may be used to evaluate the effects of genetic perturbations on induced pluripotent stem cell (iPSC) differentiation.

Unlike in current genetic screens, some embodiments provided herein can elucidate subtle changes in cellular states and especially transcriptional dynamics. For example, the methods and compositions provided herein may be used for mapping the role of genetic factors on iPSC pluripotency and differentiation. In some embodiments, these screens may be established based on both targeted gene knockouts and gene regulation to obtain complementary genetic and epigenetic insights.

Some embodiments provided herein can engineer and deconvolve multiple genetic perturbations per cell, opening an avenue to systematically elucidate the interactions between pathways and co-dependencies of genes. For example, some embodiments may be used for de novo mapping the functional gene networks during iPSC differentiation.

In some embodiments, the methods and compositions provided herein may be used to develop a highly multiplexed genome engineering method to perform systematic disruption of SNPs or allelic deletions of whole enhancers adjacent to GWAS hits, and examine their potential functional effects in vivo using a mouse teratoma model. This unique strategy allows evaluation of the functions of these regions across multiple cell types. In some embodiments, the methods and compositions provided herein may be used for characterization of at least 1000 SNPs and enhancer segments in cells of all the three developmental germ layers per single experiment.

Differences in our individual genomes give rise to most human diversity, including the susceptibility to diseases. Unraveling the precise code of the temporal-spatial execution of the human genome and consequences of sequence variations on phenotype will have tremendous impact on our understanding of normal and diseased human states. Such an understanding will also enable programming the genome for medicinal and technological purposes. Indeed a variety of powerful approaches have been employed towards deciphering the human genetic code. These include the Encyclopedia of DNA Elements (ENCODE) consortium projects that seek to identify functional genetic elements by correlating output with sequence data, and the Genome Wide Association Studies (GWAS) that have revealed large numbers of sequence variants associated with human diseases (Consortium EP. 2004, Klein et al. 2005a). Most recently with the advances in genome engineering tools, in particular the CRISPR-Cas9 (Mali et al. 2013a Nat Methods, 10(10): 957-963, Cong et al. 2013 Science. 2013; 339(6121):819-823, Jinek et al. 2013 eLife, 2: e00471) systems, we now have powerful approaches that also enable interpretation of how DNA elements act in new contexts or when mutated. Taken together, this advent of next generation genome engineering and sequencing technologies is enabling an unprecedented ability to both perturb DNA elements and assay the consequences of these perturbations.

Figure 5:
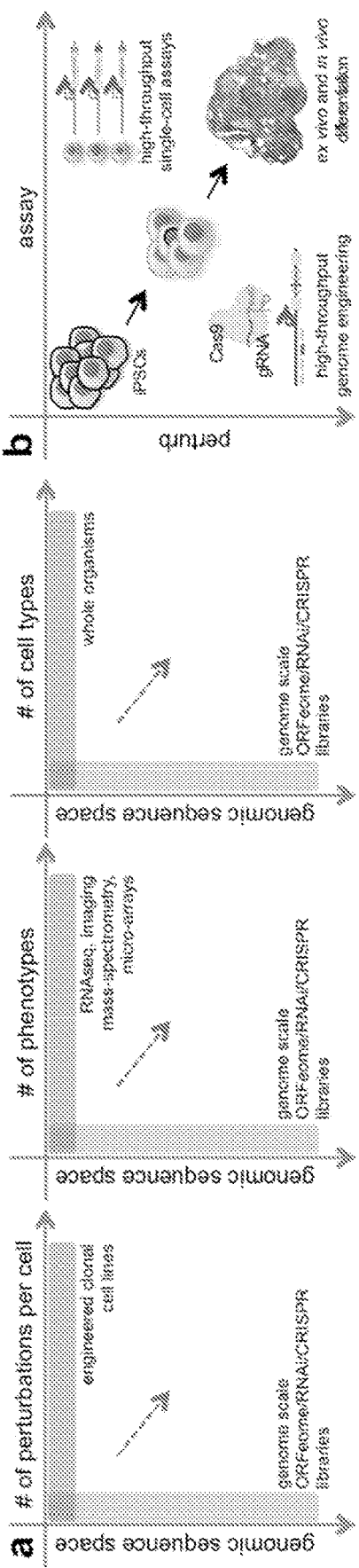
FIG. 5. (a) Current genetic screening approaches such as those based on ORFeome, RNAi and CRISPR libraries are fundamentally limited in their capabilities on three key fronts: one, engineering and de-convolving multiple perturbations per cell; two, assaying multiple cellular phenotypes; and three, accessing phenotypic information across diverse cell types of all three germ layers. Notably, while the first aspect can be achieved in a clonal cell population, and the second is feasible via RNAseq, imaging, mass-spectrometry, and micro-array based methodologies, coupling these multi-parameter phenotypic readouts to high-throughput combinatorial genetic perturbations remains a central challenge using any existing technology platform. Furthermore, on the third aspect, broad phenotypic analysis is only feasible by exploring a few perturbations at a time via assays in whole model organisms. (b) Towards these, provided here is an embodiment to enable high-throughput cum high-resolution genotype-phenotype mapping in physiologically relevant contexts. This embodiment facilitates integration of the massively scalable and multiplexable genome engineering capabilities of the CRISPR-Cas systems with single-cell genome-scale transcriptomic and epigenomic assaying technologies. Further provided is a strategy whereby genomically perturbed iPSCs are differentiated to a teratoma, thus enabling effective evaluation of functions of genomic elements across multiple cell types for all the three germ layers.

However unraveling the genetic code entails exploring a genomic sequence space and combinations thereof that is vast, and fine-mapping of the consequences of targeted genetic perturbations. In this regard we remain fundamentally bottlenecked by lack of facile approaches that couple genetic perturbations with comprehensive phenotyping at a massive scale. Genetic variants that have more subtle phenotypic consequences, which might represent the majority, are not amenable to current screening strategies. In fact most genetic screens typically assay only a few phenotypes such as cell survival or growth rate (Boutros et al. 2008 Nat Rev Genet, 9(7): 554-566, Liberali et al. 2015 Nat Rev Genet, 16(1): 18-32, Shalem et al. 2015 Nat Rev Genet, 16(5): 299-311) as cells from screens are usually bulk harvested for analysis at the end of the selection process, and consequently the transcriptomic or proteomic changes associated with the specific perturbations are rendered inaccessible (FIG. 5a). Thus, it is desirable to have genetic screening methodology which enables both large-scale combinatorial genetic perturbations and corresponding multi-parameter phenotypic evaluations in their native physiological contexts. By integrating the massively multiplexable and scalable genome engineering capabilities of the CRISPR-Cas9 systems (Mali et al. 2013c Science, 339(6121): 823-826, Cong et al. 2013 Science. 2013; 339(6121):819-823, Shalem et al. 2014 Science, 343(6166): 84-87, Wang et al. 2014 Science, 343 (6166): 80-84) with single-cell transcriptomic and epigenomic assaying technologies (Gole et al. 2013 Nat Biotechnol, 31(12): 1126-1132, Klein et al. 2015 Cell, 161(5): 1187-1201, Macosko et al. 2015 Cell, 161(5): 1202-1214), some embodiments set forth herein provide such an approach (FIG. 5b). In some embodiments, a CRISPR-Cas9 design is utilized whereby genetic modifications and transcriptome information in individual cells are linked via RNA barcodes. This allows aggressive multiplexing not only on the number of genetic changes but also different cell types. In some embodiments, iPSC differentiation to teratomas (Lensch et al. 2007) may be used to effectively evaluate functions of genomic elements across multiple cell types for all three germ layers (Evans M. 1981 J Reprod Fern', 62(2): 625-631, Martin G. R. 1981 Proc Natl Acad Sci USA, 78(12): 7634-7638, Takahashi et al. 2007 Cell, 131(5): 861-872, Takahashi et al. 2006 Cell, 126(4): 663-676, Thomson et al. 1998 Science, 282(5391): 1145-1147, Yu et al. 2007 Science, 318(5858): 1917-1920, Lancaster et al. 2014 Science, 345(6194): 1247125, Mali et al. 2012 Stem Cells, 30(1): 75-81). In some embodiments, the methods and compositions provided herein may be used for examining the transcriptomic consequences of 1000-10,000 genetic modifications per single experiment. Treating the single-cell transcriptome as a phenotype opens up the possiblity of screening traits that cannot be easily connected to cell growth, survival, or fluorescent reporters. This will greatly accelerate the pace and expand the scope of experimental annotation of functional elements and variants in the human genome. The mouse terotoma screening strategy allows characterization of cell-type specific effects, on many cell types representative of all three germ layers, again in a single assay. This screening method scales well with the ever increasing power of DNA sequencing, digital fluidics, combinatorial barcoding and labeling of molecules and cells. It can be used to tackle more and more complex networks, and characterize variants with very subtle or complex effects.

As shown in in FIG. 5(a), current genetic screening approaches such as those based on ORFeome, RNAi and CRISPR libraries are fundamentally limited in their capabilities on three key fronts: one, engineering and de-convolving multiple perturbations per cell; two, assaying multiple cellular phenotypes; and three, accessing phenotypic information across diverse cell types of all three germ layers. Notably, while the first aspect can be achieved in a clonal cell population, and the second is feasible via RNAseq, imaging, mass-spectrometry, and micro-array based methodologies, coupling these multi-parameter phenotypic readouts to high-throughput combinatorial genetic perturbations remains a central challenge using any existing technology platform. Furthermore, on the third aspect, broad phenotypic analysis is only feasible by exploring a few perturbations at a time via assays in whole model organisms.

As shown in FIG. 5(b) in one embodiment an approach is provided herein to enable high-throughput cum high-resolution genotype-phenotype mapping in physiologically relevant contexts. This approach may integrate the massively scalable and multiplexable genome engineering capabilities of the CRISPR-Cas systems with single-cell genome-scale transcriptomic and epigenomic assaying technologies. In some embodiments, genomically perturbed iPSCs are differentiated to a teratoma, thus enabling effective evaluation of functions of genomic elements across multiple cell types for all the three germ layers.

Some embodiments provided herein integrate cutting-edge technologies in three areas: genome engineering, single-cell genomics analyses and stem cell assays. In some embodiments, a barcoding strategy to directly couple the presence of gRNAs in a cell (the genotype) to the corresponding transcriptomic state (the phenotype) is provided. By scaling this to gRNA libraries and to droplet-based analyses on tens of thousands of cells, a genotype-phenotype mapping platform of unprecedented scale and resolution may be provided. Notably this barcoding and assaying strategy is also versatile and can be extended to RNAi, ORFeome and other screening systems. Unlike contemporary genetic screens, some embodiments also enable two major methodological advances towards interpreting the human genome: (i) massive scale assaying of genetic elements and variants that have un-screenable phenotypes (subtle effects, loss of cell identity or gain of diversity, pleiotropic effects) is now made feasible, thus opening an avenue to exhaustively explore coding and non-coding regions for their functions; (ii) engineering and de-convolving of multiple genetic perturbations per cell is also now made feasible, thus opening an avenue to systematically elucidate the interactions between pathways and co-dependencies of genes. Some embodiments provide a strategy to access phenotypic information that utilizes iPSC differentiation to a teratoma thus allowing us to effectively evaluate functions of genomic elements across multiple cell types for all the three germ layers. This is particularly relevant to genetic variants underlying susceptibility to complex diseases, because the cell types of interest might not be immediately obvious.

The compositions and methods described herein provide a powerful next-generation functional population genetics technology that complements sequencing-based hypothesis generation capacity. Some embodiments provided herein integrate CRISPR-Cas9 based genome engineering with droplet based single-cell genomics methodologies and associated computational analyses.

The prokaryotic CRISPR-Cas systems can be engineered to function robustly as a RNA-guided genome-editing tool in many eukaryotic cells (Mali et al. 2013c, Cong et al. 2013, Jinek et al. 2013). In this system a guide-RNA (gRNA), in complex with a protein Cas9, targets genomic sequences homologous to the gRNA. Targeting new genomic sequences simply entails modifying the gRNA sequence, thus enabling a range of targeted and multiplexed genome editing and regulation capabilities (Mali et al. 2013a Nat Methods, 10(10): 957-963, Price et al. 2015 Proc Natl Acad Sci USA, 112(19): 6164-6169). Some embodiments provided herein relate to a next-generation functional genetic screening method that integrates the CRISPR-Cas9 systems with single-cell genome-scale transcriptomic assaying technologies (FIG. 6), thereby enabling an information-rich, multi-dimensional readout of the influence of engineered perturbations. In some embodiments, to link genetic modifications to transcriptome information in individual cells, a CRISPR lentiviral library in which each gRNA also bears a distinct RNA barcode and a 3' poly(A) sequence may be utilized. This design enables the gRNA to be detected via standard RNA capture and sequencing approaches used in single-cell assays. The resulting CRISPR library may then be delivered into cells at, notably, a user-defined multiplicity of infection (MOI) to engineer single or multiple genetic perturbations per single cell. To enable multi-parameter phenotyping, single cells may be assayed at the genome-scale for their transcriptomic signature, and the corresponding genotype may be revealed via detection of the associated RNA barcodes. The functional implications of perturbation of a gene or set of genes will be a product of not just the intrinsic properties of the genes but also of the entire cell-level context in which these are expressed. Thus analyzing both the relative distributions of the gRNAs in the whole cell population and the corresponding genome scale transcriptomic signature at the single-cell level provides an unprecedented system to unravel their single or combinatorial effects. In some embodiments, the methods and compositions provided herein may be used to evaluate the effects of genetic perturbations on induced pluripotent stem cell (iPSC) differentiation.

Figure 6:
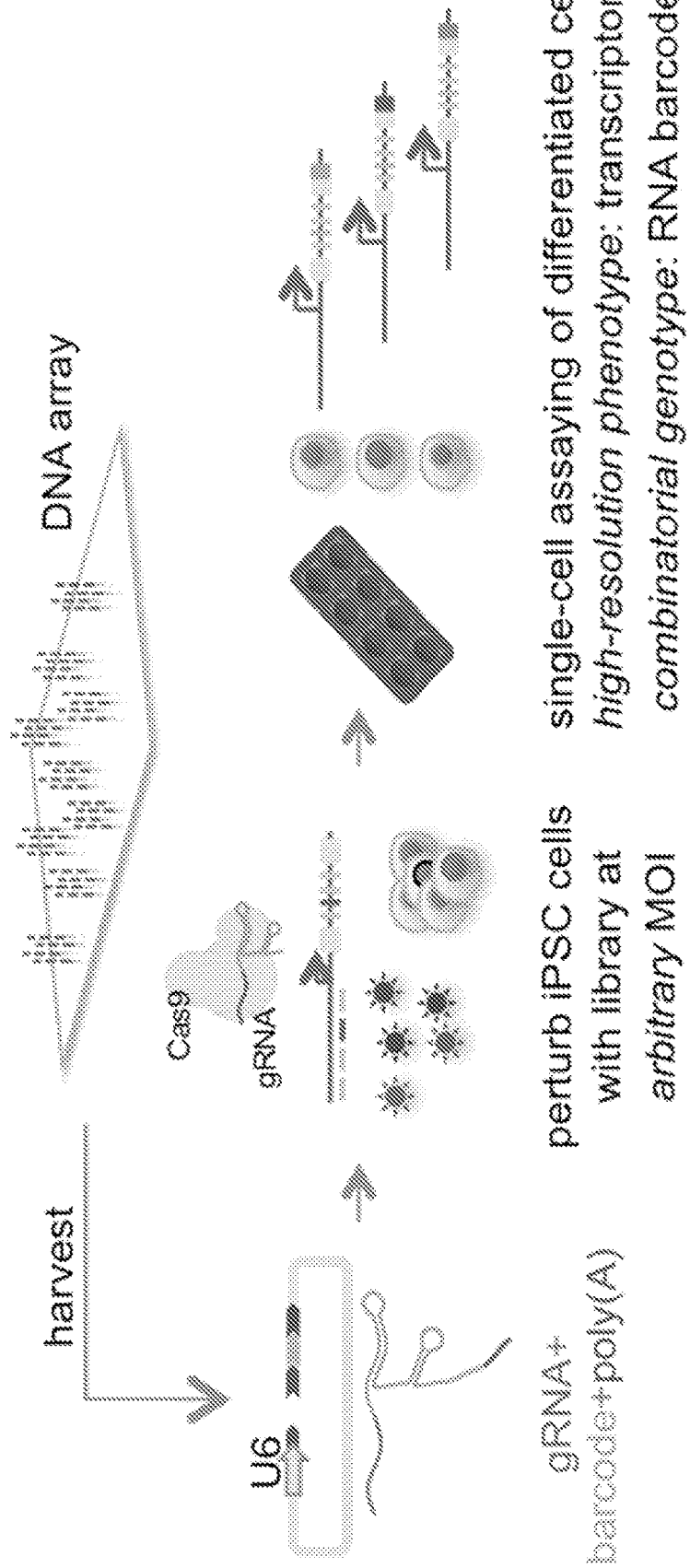
FIG. 6. In one embodiment, to integrate the massively scalable and multiplexable genome engineering capabilities of the CRISPR-Cas systems with single-cell genome-scale transcriptomic and epigenomic assaying technologies a CRISPR lentiviral library in which expression of each gRNA is coupled to the expression of a surrogate RNA barcode and 3' poly(A) tail is engineered. The resulting CRISPR library is delivered into cells at a user defined MOI to engineer single or combinatorial genetic perturbations. To enable multi-parameter phenotyping single cells are assayed at the genome-scale for their transcriptomic signature. Corresponding genotype is revealed via detection of the associated RNA barcodes in the same individual cells.

FIG. 6 illustrates an embodiment of and exemplary method for evaluating the effects of genetic perturbations. To integrate the massively scalable and multiplexable genome engineering capabilities of the CRISPR-Cas systems with single-cell genome-scale transcriptomic and epigenomic assaying technologies a CRISPR lentiviral library in which expression of each gRNA is coupled to the expression of a surrogate RNA barcode and 3' poly(A) tail may be utilized. The resulting CRISPR library is delivered into cells at a user defined MOI to engineer single or combinatorial genetic perturbations. To enable multi-parameter phenotyping single cells are assayed at the genome-scale for their transcriptomic signature. Corresponding genotype is revealed via detection of the associated RNA barcodes in the same individual cells.

Current high-throughput pooled screening approaches rely on phenotypes that can be coupled to cell survival, fluorescent cell sorting, or affinity enrichments. Genetic variants that have more subtle phenotypic consequences are not amenable to such screens. By treating the full transcriptome of a single cell as the phenotype, any genetic perturbation that leads to systematic transcriptional changes becomes detectable. By coupling CRISPR/Cas9 library screening with massively parallel single-cell transcriptome sequencing using droplets, a platform for rapid and large-scale cataloging of gene functions is provided. Such an approach will pave the way for unprecedented systematic, in-depth, and highly quantitative studies of genotype-phenotype relationships.

One embodiment relates to quantitative characterization of the transcriptional response of individual cells each carrying different CRISPR-Cas engineered genetic modifications at a massive scale.

In some embodiments, CRISPR-Cas9 design compatible with single-cell RNA sequencing may be utilized, such that the sequencing data from each cell contain information of both the genetic modification and its functional outcomes in the form of transcriptome profile. Towards this end a gRNA design that is detectable with standard RNA capture and sequencing approaches used in single-cell assays, and also compatible with lentiviral production may be utilized. An exemplary gRNA design is outlined in FIG. 7a. This optimized design bears a 12 bp random barcode and a 25 bp 3' poly(A) tail. The chimeric crRNA-tracrRNA hairpin is further mutagenized to eliminate poly(T)s that serve as transcriptional pauses for U6, also bears a short extension to stabilize the hairpin to accommodate a Tn5 consensus recognition motif in the loop region. To validate this engineered design, two lentiviral constructs were constructed, each bearing the same guide-RNA spacer sequence targeting the AAVS1 locus, but one based on the poly(A) tail architecture and the other based on the conventional gRNA scaffold. Furthermore, each construct was also designed to include a downstream GFP cassette under the control of a PGK promoter. Both constructs were packaged and stably delivered into 293T cells along with a Cas9 expressing lentivirus and assayed for functionality via multiple independent assays: 1) Presence of the poly(A) tail was important to enable detection of gRNAs after RT-PCR when using oligo-d(T) capture probes (FIG. 7b). This was an important aspect to establish as droplet based single-cell assays utilize oligo-d(T) coated beads for transcriptome capture. The poly(A) gRNA design, importantly, retained similar functionality with respect to the conventional design as assayed by their ability to introduce non-homologous end joining (NHEJ) mediated in-dels at the AAVS1 locus (FIG. 7c). Presence of a poly(A) sequence did not compromise lentiviral titer, as equal amounts of virus from each prep gave comparable GFP signal from the downstream PGK-GFP cassette (FIG. 7d). This was an important aspect to confirm as lentiviral constructs typically do not bear poly(A) signals to ensure the full-length RNA genome is efficiently transcribed.

Figure 7:
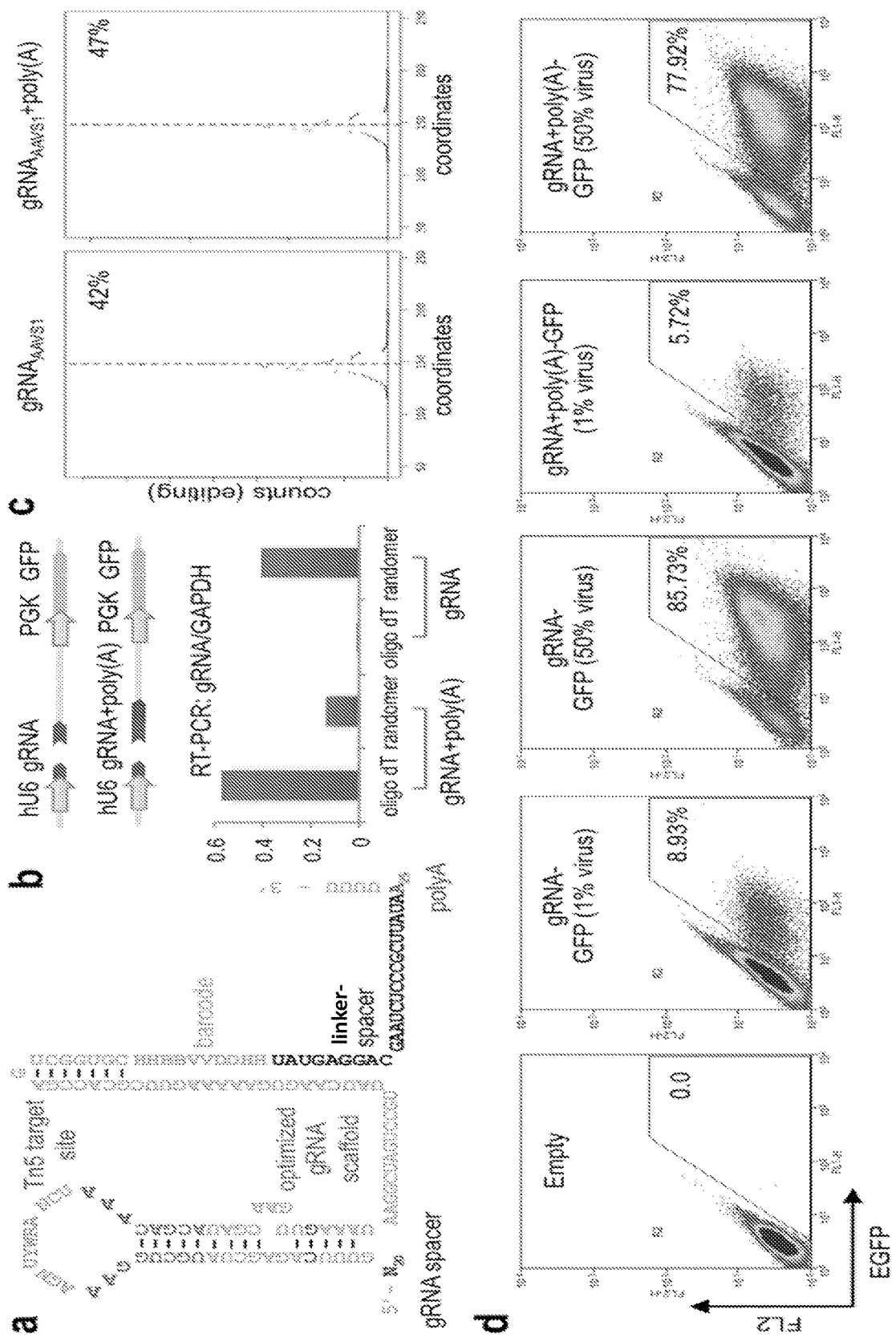
FIG. 7. (a) Schematic of an embodiment of an exemplary engineered gRNA design that is detectable with standard RNA capture and sequencing approaches used in single-cell assays. The nucleotide sequence shown corresponds to SEQ ID NO: 1. The barcode sequence may be completely arbitrary. In some instances, a pattern in the barcode sequence may be chosen so that there is an underlying pattern to the barcode. For example, the barcode shown (HHBBVVD-DHH) may have any nucleotide present at each position or there may be an underlying pattern. (b) Schematic of an embodiment of two lentiviral constructs with or without gRNAs bearing a poly(A) sequence to functionally validate the design. RT-PCR confirmed that in this embodiment, the presence of the poly(A) tail was needed to enable detection of gRNAs via oligo-d(T) capture probes (c) NGS analysis of NHEJ mediated in-del rates confirmed the poly(A) design retained similar genome-targeting functionality. (d) Finally, detection of comparable GFP signal from the downstream PGK-GFP cassette from both lentiviral constructs confirmed that presence of a poly(A) in this embodiment did not compromise lentiviral titer.

FIG. 7 (a) provides a schematic of an embodiment of an engineered gRNA design that is detectable with standard RNA capture and sequencing approaches used in single-cell assays. FIG. 7(b) provides a schematic of an embodiment of two lentiviral constructs with and without gRNAs bearing a poly(A) to functionally validate the design. Indeed RT-PCR confirmed that presence of the poly(A) tail was needed to enable detection of gRNAs via oligo-d(T) capture probes. NGS analysis of NHEJ mediated in-del rates confirmed the poly(A) design retained similar genome-targeting functionality (FIG. 7(c)). Detection of comparable GFP signal from the downstream PGK-GFP cassette from both lentiviral constructs confirmed that presence of a poly(A) sequence did not compromise lentiviral titer (FIG. 7(d)).

Figure 8:
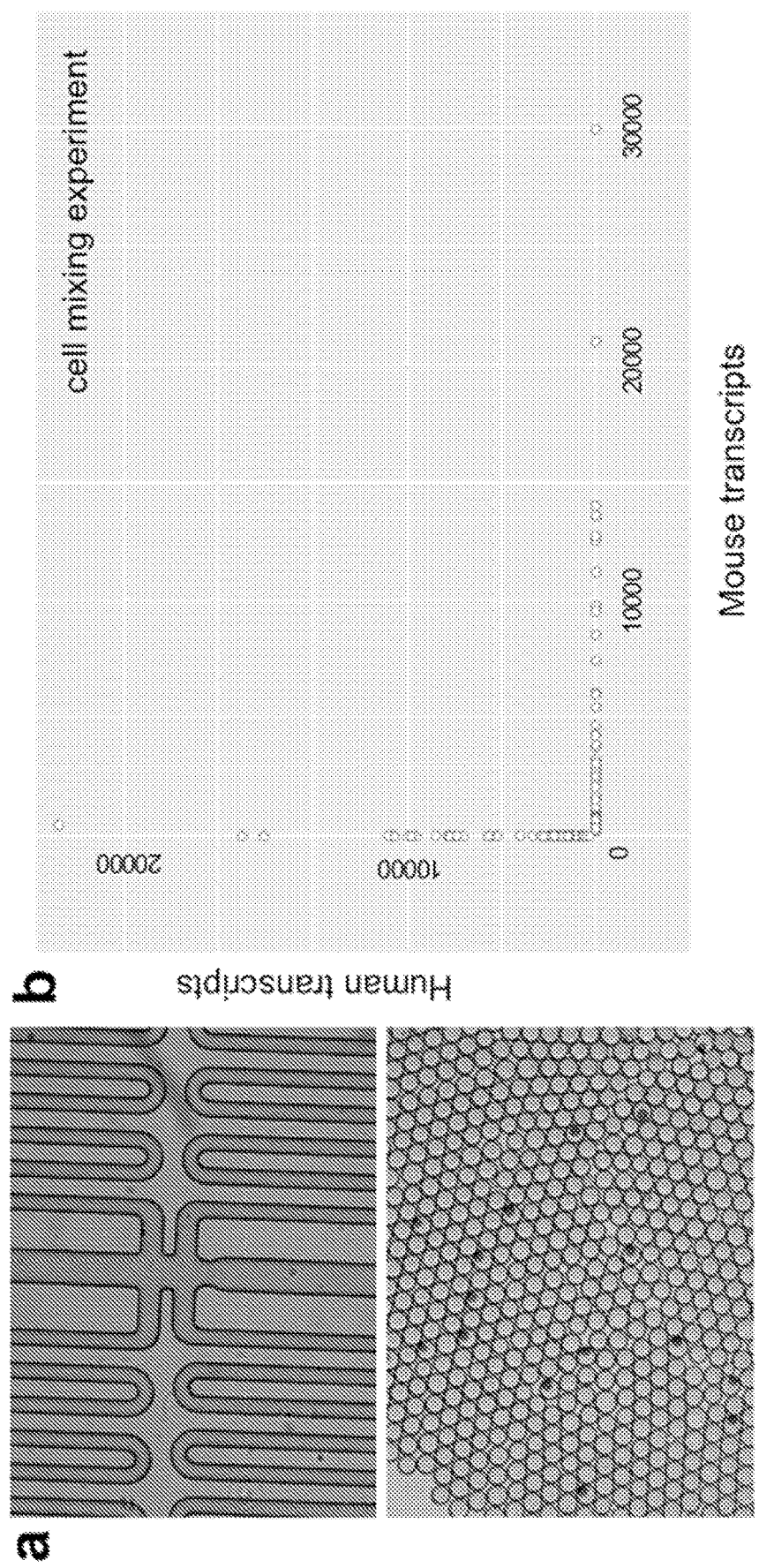
FIG. 8. (a) An embodiment of an in house fabricated PDMS microfluidic chips for droplet formation. (b) Demonstration of feasibility of an embodiment of an accurate sequencing of the single-cell transcriptome from a mixture of human (293T) and mouse (3T3) cells.

In some embodiments, production-scale single-cell RNA sequencing may be performed using the Fluidigm C1 platform, and more recently has implemented two droplet-based methods, Drop-Seq (Macosko et al. 2015 Cell, 161(5): 1202-1214) and In-Drop (Klein et al. 2015 Cell, 161(5): 1187-1201). In some embodiments, PDMS microfluidic chips for droplet formation may be manufactured, and can consistently produce droplets with barcoded beads and cells at a success rate comparable to Drop-Seq (FIG. 8a). In some embodiments, a combination of flow speed and surfactant concentration may be utilized that allows generation of droplets at 50% smaller volume, which essentially doubles the concentration of RNA molecules after cell lysis and improves the capture efficiency by bead-bound poly(T) primers (FIG. 8b). In some embodiments, the gDNA barcoding scheme may be coupled with the Drop-Seq protocol, and used for sequencing both the gDNA barcodes and the transcriptome from the same single cells. In some embodiments, the In-Drop method, which is more efficient in packaging single cells (single Poisson distribution versus double Poisson with Drop-Seq), and potentially more sensitive in RNA capture with the UV cleavable poly(T) primers (Junker et al. 2015 Mol Cell, 58(4): 563-564) may be utilized. As single-cell sequencing technologies are rapidly evolving, newer platforms (such as 10× Genomics' GEM, Bio-Rad) may also be used if they can provide a higher throughput or better sensitivity in capturing single RNA molecules. In some embodiments, at least 50 single cells may be covered at 20,000 sequencing reads per cell for each successful genetic modification. A screen of 5,000 editing targets can be accomplished with the current capacity of three HiSeq4000 sequencing flow-cells. Coupled with the gRNA design optimization, between 5-15% of the total RNAseq reads are routinely observed to be from the gRNA-poly(A) transcript, thus enabling robust mapping of genotype and transcriptome phenotype across a range of sequencing depths.

FIG. 8a illustrates an embodiment of a fabricated PDMS microfluidic chips for droplet formation. FIG. 8(b) demonstrates feasibility of accurate sequencing of the single-cell transcriptome from a mixture of human (293T) and mouse (3T3) cells.

Towards downstream analysis, computation on single-cell RNA sequencing data may be performed at three levels. First, from the raw sequencing data we will perform read decoding, mapping, gene expression quantification and assignment of different Cas9 modifications to single-cell transcriptome data sets. Such low-level data processing produces a big matrix per experiment, which contains 5,000-10,000 rows (genes) and 50,000+ columns (cells). In additional, each column (cell) may have a label, which corresponds to a particular genetic modification made to the cell. The computational tools required for this part of processing are all in place. In some embodiments, single-cell transcriptome analysis of human brains may be performed using the methods and compositions provided herein. A computational pipeline for automatic processing of tens of thousands of single-cell transcriptome data sets, reporting various QC metrics and quality filtering are already in place on the TSCC cluster housed by the San Diego Supercomputer Center. The second level of analysis may start with large and relatively sparse data matrices, and computationally partition all cells into clusters in distinct transcriptional states. There are multiple computational methods for this purpose, including PAGODA, or other published methods (Monocle (Trapnell et al. 2014 Nat Biotechnol, 32(4): 381-386), Seurat (Satija et al. 2015 Nat Biotechnol, 33(5): 495-502), RaceID (Grun et al. 2015 Nature, 525(7568): 251-255). The most appropriate method will depend on the nature of transcriptional responses. For example, if the cells fall into several clearly separated and discrete cell states, the iterative clustering & classification strategy developed for the SCAP-T project (Lake et al, submitted) or Seurat would be applicable. If the responded cells represent a rare sub-population, outlier analysis such as the one implemented in RaceID could be more sensitive. On the other hand, if cells respond to the genetic modifications by migrating on certain trajectories along the transcriptional landscape without grouping into clearly separated clusters, Monocle could be particularly powerful. Eventually, each transcriptome data set in the matrix will be assigned to a cluster, or in the case of Monocle, a pseudo-time value assigned along the population trajectory.

In some embodiments, the effects of individual genetic modifications on transcriptional phenotypes are characterized. In some embodiments, on average >40 single cells may be sequenced per each genetic modification and each condition. In the most optimistic situation, the majority of cells with one particular modification will fall into one cluster (or one narrow pseudo-time interval) identified above, in which case standard differential gene expression analysis could be sufficient. Based on the combinatorial expression patterns of several well-understood genes, a biologically meaningful description (functional annotation) of the cell cluster and the effect of the genetic modification may be provided. Note that PAGODA (Fan et al. Nature Methods in press), which extended the principle of gene-set enrichment analysis to variably expressed network among single cells, is particularly powerful for identifying genetic modifications that affect multiple pathways (including controlling cell-cycle effects). In the situation where the transcriptional response to a genetic modification is less homogeneous among different cells, or more subtle to push the cells to a less clearly identifiable cellular state, iterate over all the genetic modifications may be utilized to determine whether each modification is enriched in one or a few cell clusters, or certain domain along the pseudo-time axis, over a null distribution generated by the permutation. In another situation along this direction, a genetic modification (i.e. epigenetic regulators) can potentially cause the loss of a cell's identity, similar to what has been observed in cancer (Hansen et al. 2011 Nat Genet, 43(8): 768-775). In this case, the compactness of all cells carrying a specific modification is a quantitative phenotype, which is not amenable to existing screening strategies, but can be analyzed within a formal statistical framework with our method. For modifications of genes that are in proximity of known gene-gene or protein-protein interaction networks, we will also pool such genes as a group for the enrichment analysis. Some embodiments take advantage of the fact that every single-cell data set is already connected to a specific modification, and perform supervised classification of all cells based on the genetic modifications. Under this approach, in some embodiments, a small set of the most differentially expressed genes for each modification may be identified and bi-clustering may be performed on the entire collection of such genes and all cells. This enables discovery of novel interactions between modified genes (columns) and responding genes (rows) not reported in the literature.

In some embodiments, the synthesis process may be scaled up to create gRNA-poly(A) libraries by utilizing array-based oligonucleotide synthesis approaches. Some embodiments provide an integrated framework to couple CRISPR-Cas9 genome engineering and droplet based single-cell assay methodologies, and engineer corresponding gRNA libraries.

Figure 9:
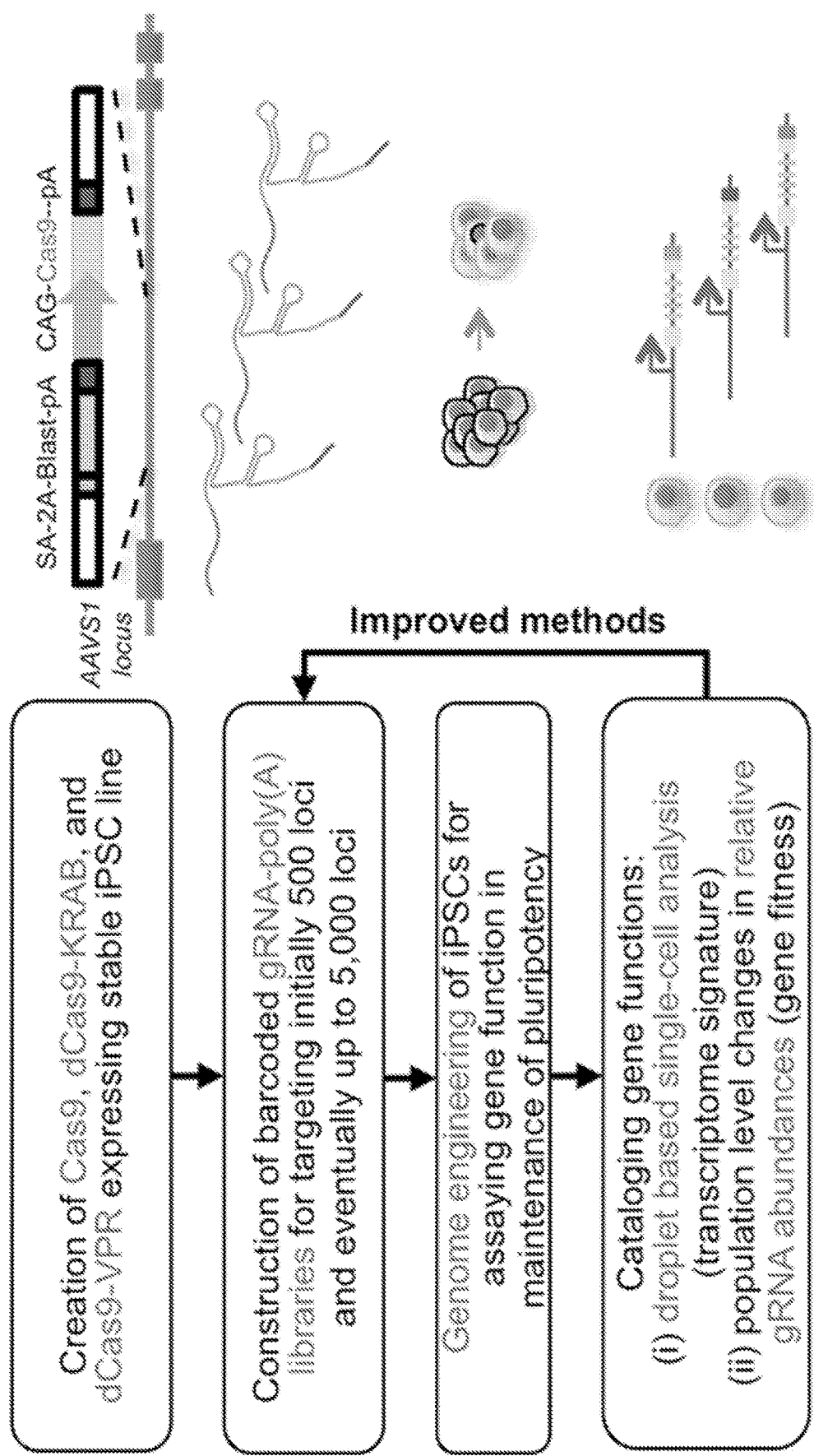
FIG. 9. Schematic of an embodiment of a proposed a roach for large-scale information-rich, multi-dimensional cataloging of gene function.

An embodiment of an exemplary procedure is provided in the schematic outlined in FIG. 9. iPSC lines are generated bearing genomically integrated Cas9 that is stably expressed from the AAVS1 locus. Poly(A) barcoded gRNA libraries are constructed as described herein, and these are in turn be used to engineer corresponding regions in the iPSCs. In some embodiments, the methods and compositions provided herein may be used to examine the role of epigenetic factors on maintenance versus exit from pluripotency of iPSCs. Single-cells are analyzed via the droplet-based approach described herein. In some embodiments, to ensure adequate library coverage, on average at least 40× single-cells are analyzed, where x is the size of the gRNA library. Similar to current pooled screening approaches bulk cells may also be analyzed for relative abundances of the gRNAs to assay relative gene fitness effects.

In some embodiments, the genetic screens re implemented based on both gene knockouts and gene regulation to obtain complementary genetic and epigenetic insights, as endogenous gene expression modulation can yield nuanced and rich information on the underlying gene function. In this regard, in some embodiments, the CRISPR-Cas toolset may be expanded by engineering additional orthogonal Cas9-gRNA systems and the methodology may be extended to enable targeted genome-regulation via use of a nuclease-null Cas9 (dCas9) fused to transcriptional repression or activation domains (Esvelt et al. 2013 Nat Methods, 10(11): 1116-1121, Mali et al. 2013b Nat Biotechnol, 31(9): 833-838, Gilbert et al. 2014 Cell, 159(3): 647-661). For repression, in some embodiments, the well-established KRAB effector (Gilbert et al. 2014 Cell, 159(3): 647-661) may be used, and for transcriptional activation the highly active chimeric VP64-p65-RtA effector fusion (Chavez et al. 2015 Nat Methods, 12(4): 326-328) may be used. Since the core gRNA library construction methodology will be identical, simply utilization of these dCas9-transcriptional effector fusions coupled with the existing computational pipeline will readily expand the scope of the screens. FIG. 9 provides a schematic of an exemplary procedure for large-scale information-rich, multi-dimensional cataloging of gene function. In some embodiments, 500 to 5,000 genomic loci may be evaluated per assay. For example, 500, 1,000, 1500, 2000, 2500, 3000, 3500, 4000, 4500, 5000 or a range defined by any two of the preceding values of genomic loci may be evaluated per assay, such as 500-1000, 1000-2000, and 2000-5000. Top functional candidates may be evaluated via targeted experiments.

Figure 10:
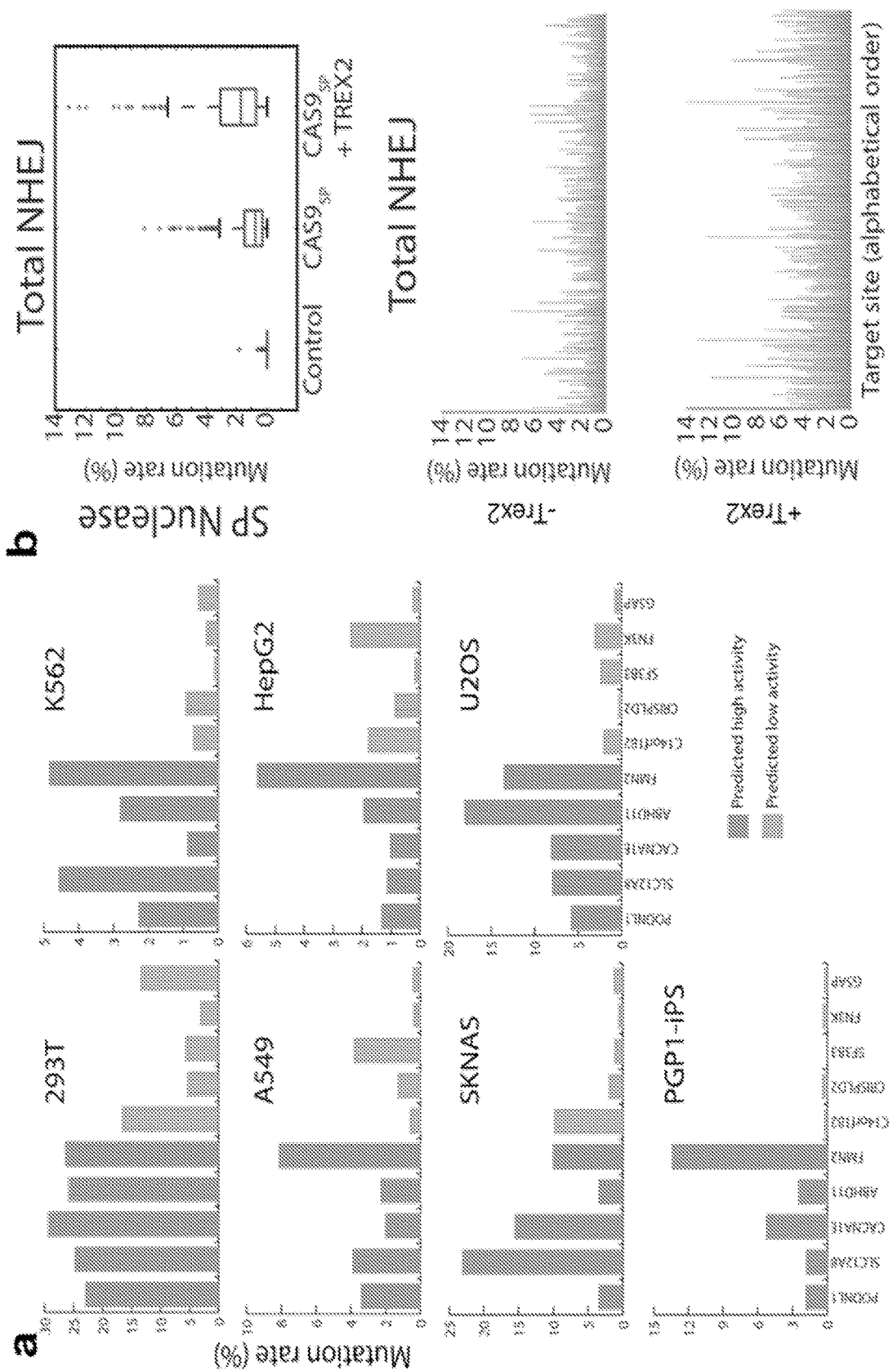
FIG. 10. (a) Efficacy of an embodiment of a SVM classifier via its ability to successfully predict high or low activity across 10 target sites and 7 cell lines. In each plot, the first five bars corresponding to PODNL1, SLC12A8, CACNA1E, ABHD11 and FMN2 are predicted high activity and the second set of five bars corresponding to C14orf182, CRISPLD2, SF3B3, FN3K and GSAP are low activity. (b) Box plot depicting the mutational diversity across 1400 tested loci (upper panel), and corresponding rates of targeting (y-axis) at each of these 1400 loci (x-axis) is depicted (lower panel). Note the addition of Trex2 significantly enhances overall NHEJ mediated gene targeting rates.

Cas9 mediated genome regulation may not be robust and induced transcriptional changes may be moderate in amplitude. In some embodiments, this can be addressed by using synergy either via multiple gRNAs or via recruitment of multiple effector domains to alleviate robustness issues (Mali et al. 2013b Nat Biotechnol, 31(9): 833-838, Chavez et al. 2015 Nat Methods, 12(4): 326-328, Konermann et al. 2015 Nature, 517(7536): 583-588, Hilton et al. 2015 Nat Biotechnol, 33(5): 510-517). 2) In some embodiments, to ensure maximum library efficacy the choice of gRNAs may be optimized not just in their specificity profile, but also in their putative activity. In some embodiments, the recently described (Chari et al. 2015 Nat Methods, 12(9): 823-826) support vector machine (SVM) classifier developed to identify the most active gRNAs may be used and coupled with screened enhancers of genome engineering processes such as Trex2 (FIG. 10). FIG. 10($a$) shows tests on the efficacy of an embodiment of the SVM classifier via its ability to successfully predict high or low activity across 10 target sites and 7 cell lines. FIG. 10($b$) provides a box plot depicting the mutational diversity across 1400 tested loci (upper panel), and corresponding rates of targeting (y-axis) at each of these 1400 loci (x-axis) is depicted (lower panel). The addition of Trex2 significantly enhances overall NHEJ mediated gene targeting rates.

Considerable effort has been invested in unraveling the complex genetic mechanisms underlying cellular processes in normal and diseased states, and recent advances in loss-of-function screening techniques have become increasingly powerful at identifying individual members of pathways. Unfortunately, these single-gene screens are often unable to provide information on the interactions between pathways and the co-dependencies of genes that ultimately drive cellular transformations. In some embodiments, to gain insights into the gene networks underlying these complex processes, the methods and compositions provided herein may be used to enable a new class of high throughput reverse genetic screening approaches that enable combinatorial deciphering of the role of both single and interacting genes via a single high throughput experiment. Some embodiments provide a method for creating dual-gRNA libraries in which each synthesized oligonucleotide encodes either one or two gRNA spacer sequences. In a complimentary approach, since some of the methods herein directly assay each cell, it also enables engineering and deconvolving of multiple genetic perturbations per cell. Thus unlike in existing pooled genetic screens where to enable the downstream analysis the library MOI must be tightly regulated to ensure ≤1 perturbation per cell is effected, some embodiments provide the opportunity to explore higher order combinatorials via simply increasing the MOI of lentiviral library infection. As the number of interactions between genes scales exponentially with the number of combinations one wishes to explore, this precludes exhaustive evaluation of arbitrarily large gene sets, and thus some embodiments provide a hierarchical screening approach: starting first from the single-gRNA CRISPR screens to map key regulators of a biological system of interest, and then focusing on the top hits to evaluate those via the combinatorial screening format to map driver genetic interactions.

Figure 11:
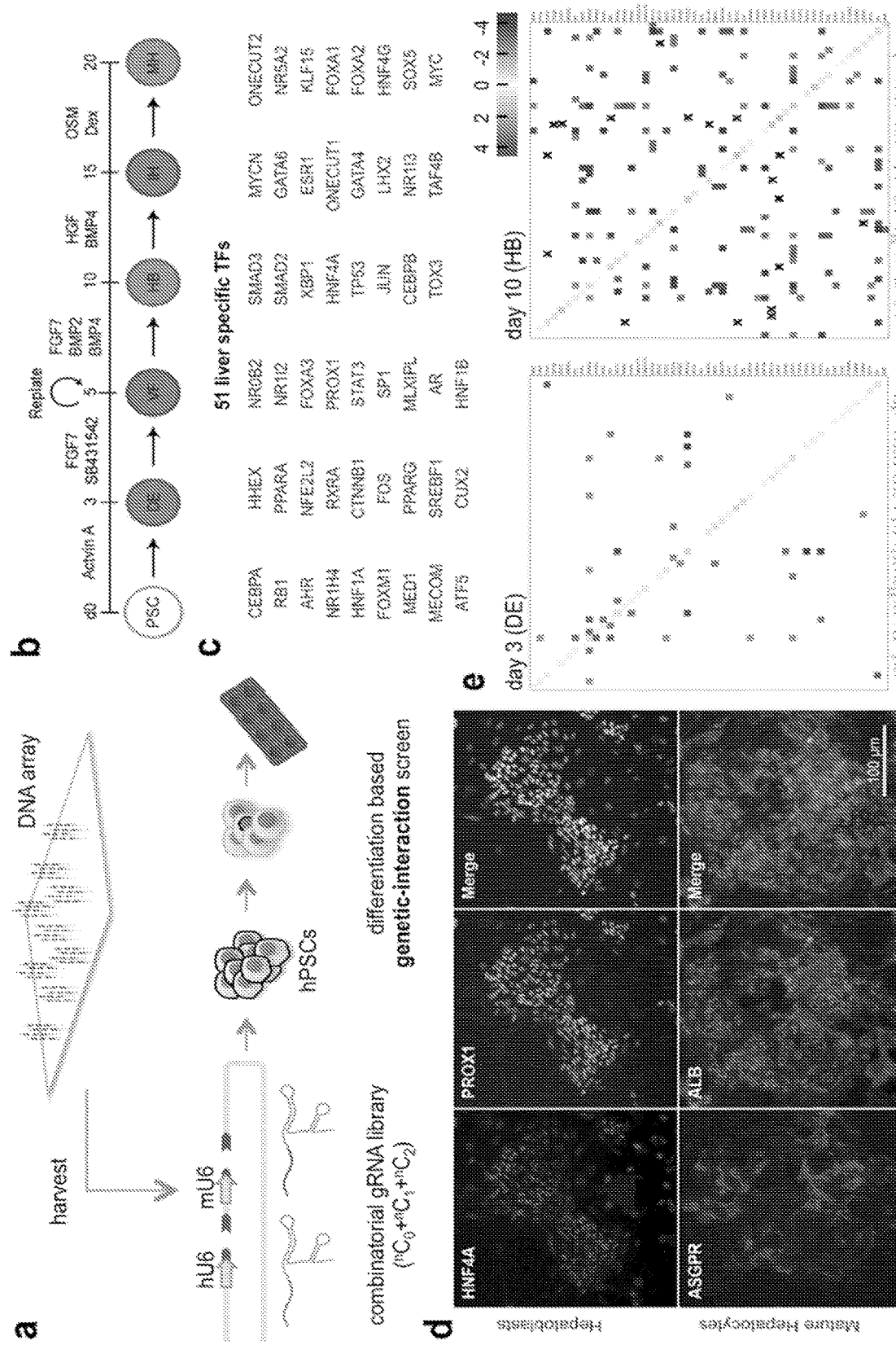
FIG. 11. (a) Schematic of an embodiment of a combinatorial genetic screening approach to de novo map functional genetic interactions during hPSC differentiation. (b) Implementation of an embodiment of an optimized 5-step hepatocyte differentiation protocol. The different stages of differentiation are depicted: DE, definitive endoderm; VF, ventral foregut; HB, hepatoblasts; IH, immature hepatocytes; MH, mature hepatocytes. (c) 51 key liver-related transcription factors (TFs) were selected based on existing literature and our current understanding of hepatic specification. (d) Representative images of immunostained differentiated cells. Scale bar=100 µm. (e) In an embodiment of a preliminary combinatorial genetic screen 1,275 interactions between these 51 liver-specific genes were analyzed in high-throughput via PSC differentiation to hepatocytes. Positive genetic interactions are plotted in red and negative interactions are shown in blue. Strongly positive genetic interactions are marked with "x".

In some embodiments, to build a systematic approach to map genetic interactions a combinatorial screening approach in hPSCs using pooled CRISPR-Cas9 dual-gRNA libraries is provided (FIG. 11$a$) where each library element encodes either one or two gRNAs (to assay single and double gene knockout effects). As an exemplar, differentiation to hepatocytes from hPSCs may be used as a model system (Takebe et al. 2013 Nature, 499(7459): 481-484, Takebe et al. 2014 Nat Protoc, 9(2): 396-409, Zhao et al. 2013 Cell Res, 23(1): 157-161) (FIG. 11$b$). For example, a select list of 51 key liver-related transcription factors (TFs) (FIG. 11$c$) based on extensive curating of existing literature and current understanding of hepatic specification may be used to assay for driver genetic interactions (FIG. 7$d$). Towards this end a dual gRNA library for the above gene-set was designed and constructed to knockout all genes singly or in pairs to obtain both single gene knockout and dual-gene knockout phenotypes. The total library size is 11,450 dual-gRNA pairs, and it targets 1,275 gene-pairs via 9 dual-gRNAs per gene pair. This library was transduced in the above iPSC line and differentiated these to hepatocytes via the above protocol and sampled cells at various stages using FACS. FIG. 11($a$) provides a schematic of a combinatorial genetic screening approach to de novo map functional genetic interactions during hPSC differentiation. FIG. 11($b$) shows implementation of an optimized 5-step hepatocyte differentiation protocol. The different stages of differentiation are depicted: DE, definitive endoderm; VF, ventral foregut; HB, hepatoblasts; IH, immature hepatocytes; MH, mature hepatocytes. In FIG. 11($c$) 51 key liver-related transcription factors (TFs) were selected based on existing literature and current understanding of hepatic specification. FIG. 11($d$) provides representative images of immunostained differentiated cells. Scale bar=100 μm. FIG. 11($e$) illustrates a preliminary combinatorial genetic screen in which 1,275 interactions between these 51 liver-specific genes were analyzed in high-throughput via PSC differentiation to hepatocytes. Positive genetic interactions are plotted in red and negative interactions are shown in blue.

In some embodiments, to enable accurate quantification of genetic interactions the following approach may be utilized: for each gene pair, a distribution of predicted double knockout phenotype effects is computed assuming multiplicative interactions between all pairwise combinations of gRNAs for a gene pair. The statistical significance of a genetic interaction is determined by comparing actual dual gRNA effects to the null distribution of expected effects. Interaction scores Or scores) are computed as the average distance of dual gRNA constructs for each double knockout from the expected distribution. P-values are also computed and FDR-corrected (Mani et al. 2008). Utilizing this approach, novel positive and negative interaction gene-pairs were unraveled and predicted interactions were validated (FIG. 11$e$). For instance, as the differentiation process is initiated with Activin, it was observed that a knockout of SMAD genes and corresponding gene-pairs is deleterious. Furthermore, a greater fraction of the interactions are manifest, as expected, with progression of differentiation to a more mature hepatic fate.

Figure 12:
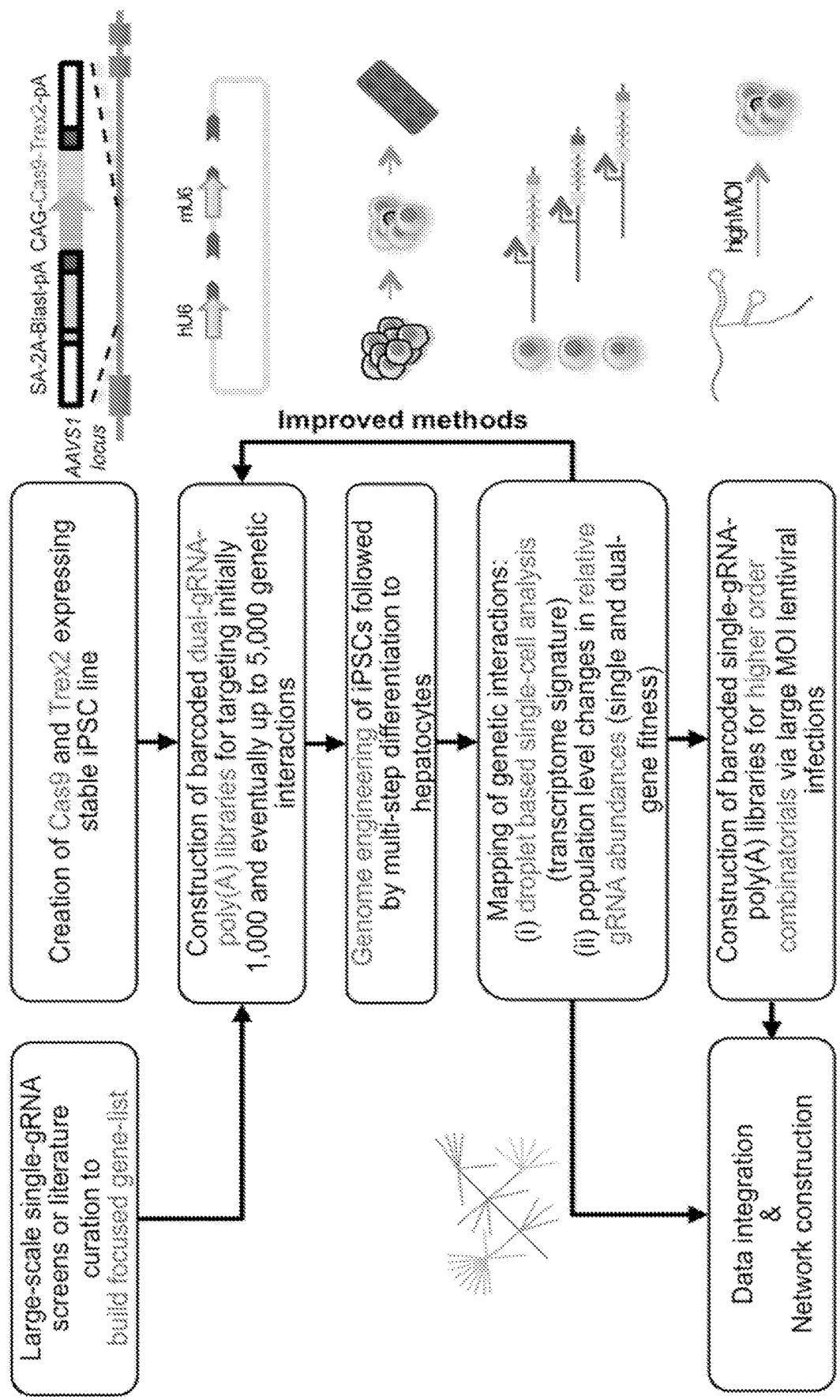
FIG. 12. Schematic of an embodiment of an exemplary approach for de novo genetic interaction mapping.

A schematic of an embodiment of an exemplary strategy is provided in FIG. 12. In some embodiments, as the number of interactions between genes scales quadratically, to ensure experimental tractability two complementary approaches may be used to build target gene lists: 1) Utilize a hierarchical screening strategy starting from single-gRNA CRISPR screens to map key regulators of a biological system of interest, and then focus on the top hits to evaluate those via this combinatorial screening format to map driver genetic interactions; and 2) leverage tissue specific pathway information and gene expression data from literature to build high-value focused gene lists. In some embodiments, iPSC lines bearing genomically integrated Cas9 and Trex2 that is stably expressed from the AAVS1 locus may be created. Poly(A) barcoded dual-gRNA libraries can be created, and these can be used to knockout corresponding genes and gene-pairs in the iPSCs. To examine their potential functional effects, in some embodiments, the methods and compositions provided herein may be used to de novo map the functional gene networks and their dynamics during iPSC differentiation to hepatocytes. Known key markers at each differentiation time-point may be utilized to enrich and assay corresponding cell populations at each stage: these include for definitive endoderm: SOX17, FOXA2, GATA4; ventral foregut: HNF4A, HNF1B; hepatoblasts: AFP, PROX1, HNF6, TBX3; immature hepatocytes: CEBPA, HNF1A; and mature hepatocytes: CYPs, ALB, AAT, ASGPR. Single-cells may be analyzed via the droplet-based approach described herein. In some embodiments, to ensure adequate library coverage, on average at least 50× single-cells may be analyzed, where x is the size of the gRNA library. FACS sorted bulk cells may also be analyzed at each stage for relative abundances of the gRNAs to compute obtain both single gene knockout and dual-gene knockout fitness effects.

While the use of the dual-gRNA library approach ensures that all possible single and double gene-pairs are perturbed exhaustively in the cell population, as, in some embodiments, the assay analyzes single cells, the MOI of infection can be increased to engineer multiplex perturbations per cell and still readily de-convolve these. In some embodiments, this approach may be utilized to evaluate higher order combinatorials where >2 perturbations per cell need to be engineered. Utilization of this approach may be particularly beneficial in scenarios when one wishes to fine-map complex pathways comprised of several gene family members with similar functions, such as isozymes in metabolic pathways.

In some embodiments, the result of these combinatorial screens provides a list of gene pairs that interact genetically. Viewing the genes as nodes, and interacting pairs as edges, a genetic interaction network limited to the candidate set may be obtained. In some embodiments, he enrichment of this sub-network may be analyzed by comparing this query network against known genetic interactions in humans and other model organisms (reference network). For humans, there is a one to one isomorphism among the nodes. The strength of the match can be tested by a composite function that rewards matching edges, and penalizes edges missing in the reference or the query network. The statistical significance of the match will be inferred by computing a P-value based on scoring edge-permuted random graphs. If the match is significant, then the edges of reference network will augment our experimentally tested edges giving a complete picture of the pathways involved in mediating the biological process.

In some embodiments, the methods and compositions provided herein may be used to characterize 1,000 to 5,000 genetic interactions per assay. In some embodiments, the top functional candidates may be validated via targeted experiments. In some embodiments, the methods and compositions provided herein may be used to identify genetic interactions that can be exploited for engineering improved iPSC differentiation towards both enhanced efficiency and maturity of derived cell types.

Since the number of interactions between n genes scales as $n^2$, in some embodiments, to ensure experimental tractability the gene list under study may be curated. Towards this end existing computational and algorithmic approaches that leverage tissue specific pathway information and gene expression data may be used to systematically evaluate and assimilate high-value gene sets (Cahan et al. 2014 Cell. 2014; 158(4): 903-915). 2) In some embodiments, multiple iPSC lines may be used as there can be inherent differences in their abilities to differentiate to certain lineages. In this scenario iPSCs derived from hepatocytes may be the best candidates for the studies. Notably ATCC does provide such a primary hepatocyte derived iPSC cell line (ATCC-HYS0103).

Despite enormous efforts by ENCODE, Roadmap Epigenomics and other consortiums, annotations of non-coding functional elements and regulatory genetic variants are mostly based on correlated analyses of enrichments. Systematic characterization of direct and causal regulatory relationships is the next frontier towards understanding the roles of numerous Variants of Unknown Significance (VUS) in normal physiology and various human genetic diseases. In some embodiments, the methods and compositions provided herein may be used to evaluate non-coding regions, by directly modifying a curated list of candidate causal SNPs and enhancers in linkage disequilibrium with GWAS hits. In some embodiments, because many regulatory regions, especially enhancers, are highly tissue specific, and cell types in which some causal regulatory variants are functioning are not immediately obvious (Gjoneska et al. 2015 Nature, 518(7539): 365-369, Zhang et al. 2013 Cell, 153(3): 707-720), a new axis may be added in the screening: injecting a library of genetically modified human iPS cells into SCID mice for teratoma formation, and sequencing single differentiated human cells from all three germ layers, to characterize the cell-type specific effects in a highly parallel manner.

The methods and compositions provided herein are generally applicable to GWAS variants of a wide variety of human diseases. In some embodiments, one may focus on a set of GWAS hits identified in the following diseases. (i) Congenital abnormalities and neonatal diseases. Genetic variants underlying this group of diseases likely have strong phenotypes during embryonic or prenatal developments, which might represent the lowest-hanging fruits for the mouse teratoma model. (ii) Heart diseases. Heart contains only a limited number of cell types, and hence serves as stepping-stones along the axis of cellular diversity before we are ready to tackle a higher level of heterogeneity. (iii) Obesity, which is likely contributed by multiple cell types in different tissues. These methods may allow discovering unexpected cell types of relevance.

FIG. 13(a) shows an embodiment of a high efficiency bi-allelic genomic deletion using two gRNAs in human iPSCs. The percentage of hThy1− cells from each gRNA pair is plotted against the size of the Thy1 deletion. gRNA pairs that included L1 or L2 are shown in black or red, respectively. FIG. 13(b) shows an embodiment of a high efficiency bi-allelic homologous recombination mediated insertion of a large DNA fragment using two guide RNAs in human iPSCs. FIG. 13(c) shows an embodiment of an exemplary approaches to multiplex screen the function of GWAS hits via either targeted SNP disruption (i) or deletion of putative enhancer regions (ii) in which they reside. These screens may be complemented with validations of thus identified top hits via targeted engineering (iii) of the SNPs using HR.

Figure 13:
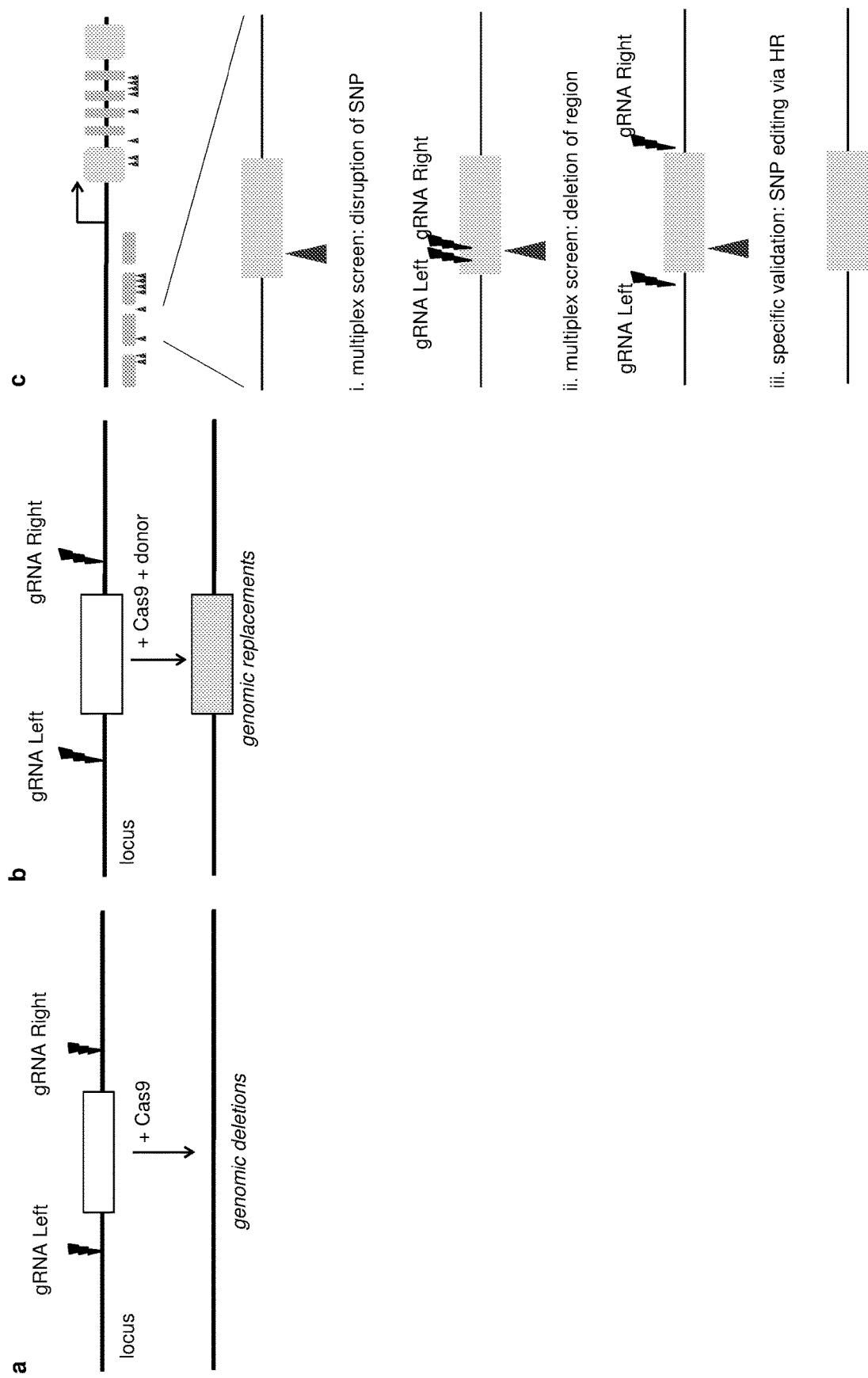
FIG. 13. (a) An embodiment of a high efficiency bi-allelic genomic deletion using two gRNAs in human iPSCs. (b) An embodiment of a high efficiency bi-allelic homologous recombination mediated insertion of a large DNA fragment using two guide RNAs in human iPSCs. (c) Multiplex screening may be performed to evaluate the function of GWAS hits via either targeted SNP disruption (i) or deletion of putative enhancer regions (ii) in which they reside. These screens may be complemented with validations of thus identified top hits via targeted engineering (iii) of the SNPs using HR.

A unique feature of the CRISPR-Cas9 system is that the gRNA design permits one to target multiple sites simultaneously by delivering more than one gRNA per cell. In some embodiments, gRNA scaffold sequences are linked to an RNA capture and sequencing domain that comprises: a barcode sequence, a primer binding sequence, and optionally a linker-spacer sequence between the barcode sequence and the primer binding sequence, as disclosed herein. In some embodiments, a linker having a certain length may be advantageous, for example in providing a length suitable for sequencing. In some embodiments the linker length is 5, 10, 15, 10, 25, 30, 35, 40, 45, 50, 75, 100, 250, 500 or 1000 nucleotides in length or a range defined by any two of the preceding values. The primer binding sequence may be any sequence to which a complementary primer can bind. In some embodiments, the primer binding sequence is conveniently a polyA sequence, which allows a gRNA to be captured alongside a cell's mRNA by reverse transcriptase when primed by an oligo-dT primer, for example during a single cell RNA-seq protocol. If the multiple sites targeted are located adjacent to each other on the same chromosome this approach can be used to effect targeted genomic deletions. This process can be very efficient in a range of cancer cell lines. More recently, this methodology has been optimized to work efficiently also in human iPSCs (Mali et al. 2013c Science, 339(6121): 823-826, Byrne et al. 2015 Nucleic Acids Res, 43(3): e21). Specifically using a dual-gRNA strategy both genomic deletions (up to a 100 kb) and genomic swaps (up to 5 kb) were efficiently engineered (FIG. 13). Notably, using this approach highly homologous genomic swaps can be engineered without the risk of intermediate crossover events, thus opening the door to efficient simultaneous introduction of multiple SNPs across several kb.

Figure 14:
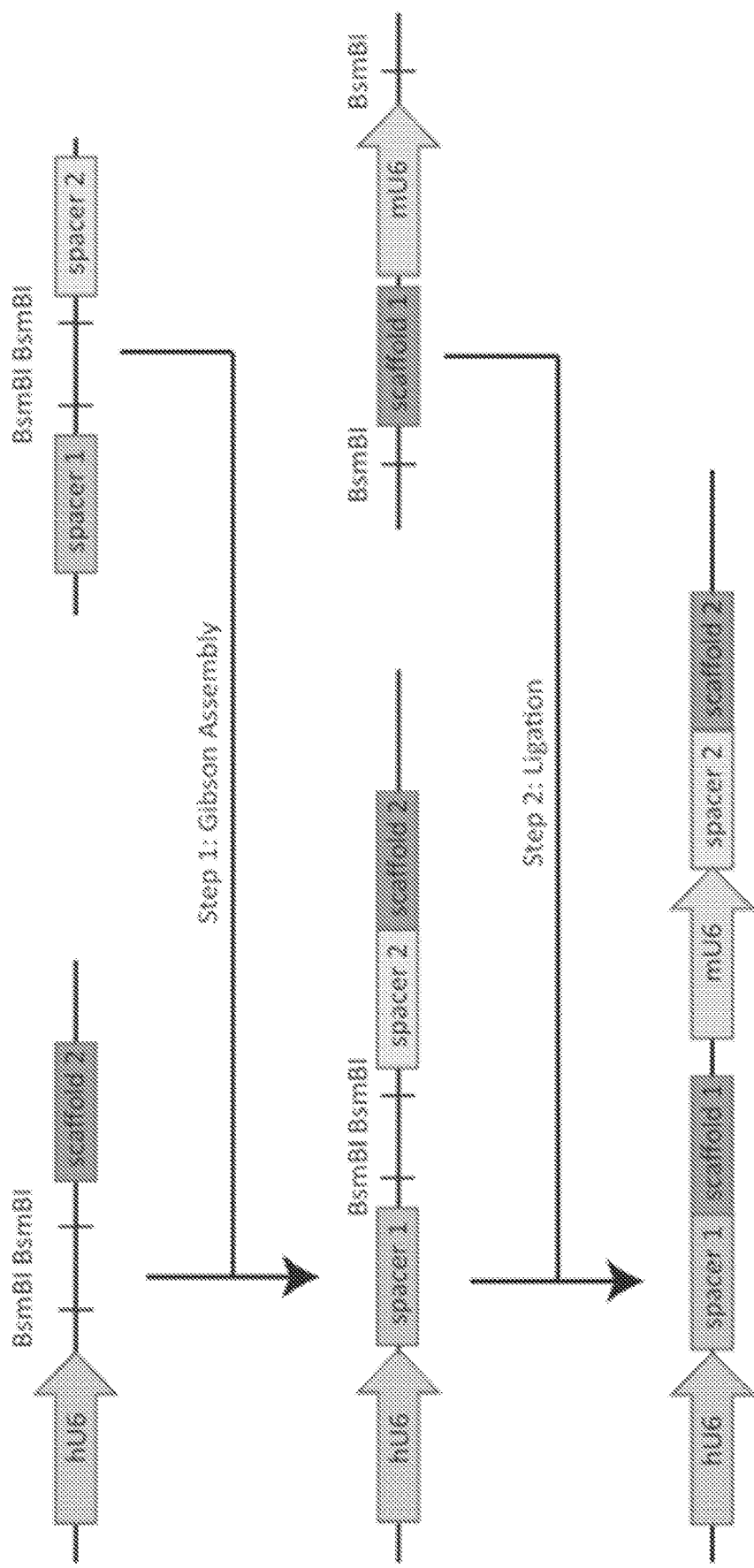
FIG. 14. An embodiment of a preparation of the dual-gRNA library involves a two-step cloning process whereby each synthesized oligonucleotide is assembled progressively with promoters and 3' gRNA scaffolds.

To scale the above process, in some embodiments, array-based oligonucleotide synthesis approaches that simultaneously produce up to 105 defined sequences may be used (Shalem et al. 2014 Science, 343(6166): 84-87, Gilbert et al. 2014 Cell, 159(3): 647-661, Konermann et al. 2015 Nature, 517(7536): 583-588, Chen et al. 2015 Cell, 160(6): 1246-1260, Sanjana et al. 2014 Nat Methods, 11(8): 783-784, Parnas et al. 2015 Cell, 162(3): 675-686), to develop a method for creating libraries in which each synthesized oligonucleotide encodes two gRNA spacer sequences. Preparation of the dual-gRNA library may be done through a two-step cloning process whereby each synthesized oligonucleotide is assembled progressively with promoters and 3' gRNA scaffolds (FIG. 14). In some embodiments, the gRNA scaffold sequences are linked to an RNA capture and sequencing domain that comprises: a barcode sequence, a primer binding sequence, and optionally a linker-spacer sequence between the barcode sequence and the primer binding sequence, as disclosed herein. This multi-step protocol may be beneficial since array based oligonucleotides from commercial vendors have a maximum length of ~200 bp, while a dual-gRNA cassette is ~1000 bp in size, thus requiring additional steps of cloning to reconstitute the full sequence. In some embodiments, the library efficacy may be optimized by eliminating the repeat sequences in the dual-gRNA vectors as these compromise both viral packaging and sequencing quality. Towards this end, the gRNA scaffold sequence was systematically mutagenized, focusing on increasing sequence diversity but keeping intact the primary hairpin loops in the gRNA scaffold via utilization of G-C vs. A-U interactions. Multiple non-homologous polymerase III promoters (hU6, mU6, H1, 7SK (Kabadi et al. 2014 Nucleic Acids Res, 42(19): e147) were analyzed and based on consistent activity hU6 and mU6 were chosen for the libraries.

FIG. 14 shows an embodiment of an exemplary approach for preparation of the dual-gRNA library using a two-step cloning process whereby each synthesized oligonucleotide is assembled progressively with promoters and 3' gRNA scaffolds.

Figure 15:
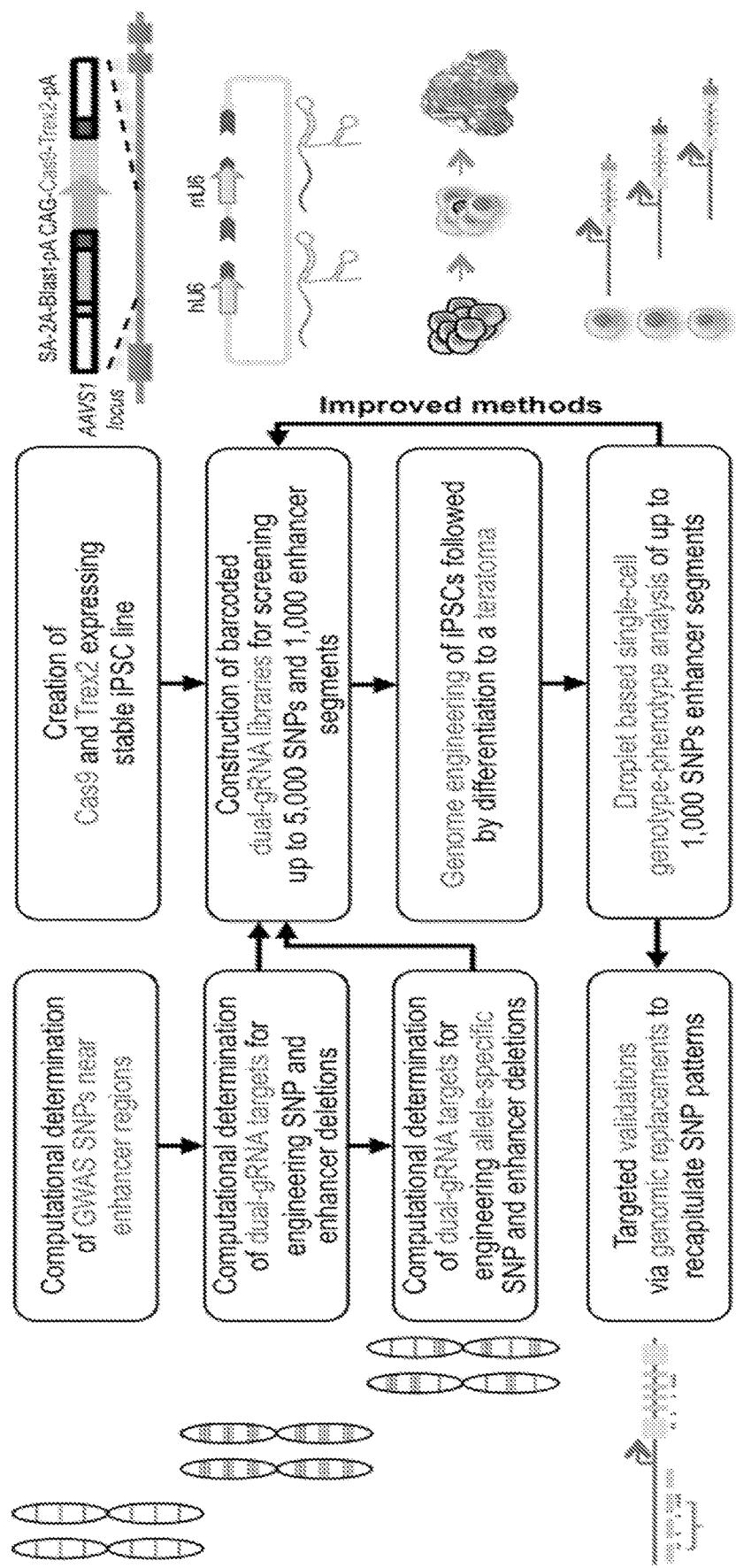
FIG. 15. Schematic of an embodiment of an exemplary approach to perform systematic disruptions of SNP regions and deletions of enhancers adjacent to GWAS hits, and examine their potential functional effects in vivo using a teratoma model.

A schematic of an embodiment of an exemplary approach for disrupting SNPs and deletions of enhancers adjacent to GWAS hits and examining their potential functional effects in vivo using a teratoma model is provided in FIG. 15. In some embodiments, this may be done using the PGP1-iPSC cell line, which for which phased whole genome sequencing information is available (Mali et al. 2013c Science, 339 (6121): 823-826, Lo et al. 2013 Genome Biol, 14(9): R100, Byrne et al. 2015 Nucleic Acids Res, 43(3): e21, Lee et al. 2009 PLoS Genet, 5(11): e1000718).

In some embodiments, ENCODE annotated enhancers that are adjacent to GWAS hits may be identified, based on the EBI GWAS catalog. Subsequently paired gRNA targets in the PGP1-iPSC genome that either target these SNPs directly or which flank enhancers adjacent to these may be determined. An initial analysis has revealed there are about 7 k, 19 k and 108 k enhancers within 2 k, 10 k and 100 k base-pair windows respectively near GWAS sites. These represent testable high value genomic elements with putative function. Utilizing the phased genome sequencing information, gRNA pairs that specifically target one allele only may be computed. This approach may utilize the fact that the *S. pyogenes* CRISPR-Cas9 system obligate requires the presence of an 'NGG' motif, the protospacer adjacent motif (PAM), after the 20 base pair guide sequence to successfully make a double stranded cut. Thus only phased SNPs that are part of a 'GG' motif, or a 'CC' motif may be included since the guide RNA can target either complementary strand. Uniqueness throughout the genome may be evaluated and the SNPs may be filtered also for haplotype phasing accuracy.

In some embodiments, PGP1-iPSC lines bearing genomically integrated Cas9 and Trex2 genes that are stably expressed from the AAVS1 locus may be generated. This choice of locus is beneficial as it is expressed in nearly all tissues in the human body, and this ensures Cas9 expression in most differentiated cells. Poly(A) barcoded dual-gRNA libraries can be constructed as described herein, and these may be used to engineer corresponding regions (bi-allelic or allele specific) in the iPSCs. In some embodiments, the cells may be differentiated in vivo to a teratoma. Single-cells from the teratoma may be enzymatically dissociated, and analyzed via the droplet-based approach described earlier. To ensure adequate library coverage, at least 1000× single-cells may be analyzed, where x is the size of the dual-gRNA library. In some embodiments, more cells per modification may be sequenced, in order to cover multiple cells types in teratoma. As a control, >10,000 single cells from teratoma generated from unmodified hiPS cells may be sequenced, and unsupervised clustering approaches may be applied to identify the number of cell types and their relative abundance. The information allows adjustment of the number of single cells to sequence in order to achieve a sufficient coverage. In some embodiments, at least 1000 SNPs and enhancer segments may be characterized per assay. Top functional candidate SNPs may be validated via targeted genomic replacement experiments in an isogenic setting.

Disruption of SNPs by NHEJ using a dual-gRNA approach is highly efficient and can be driven to near 100% completion in a cell population, however deletion of large genomic fragments (>10 kb) may be less efficient. While the use of Trex2 can greatly stimulate this process, is some embodiments, additional single-cells (up to 10× more) may be sampled to ensure adequate number of engineered deletions have been analyzed. In some embodiments, as the cell types in which certain causal regulatory variants are functioning may not be immediately obvious, at least 1000 cells from the teratoma per engineered perturbation may be assayed. In some embodiments, FACS sorting of teratoma cells may be used to enrich candidate cell types of highest interest for these assays.

Genetic interaction mapping may have wide applications such as in synthetic lethal screening in cancers and a generalizable experimental cum computational pipeline may be built.

In any of the embodiments disclosed herein, the gRNA scaffold sequences can be linked to an RNA capture and sequencing domain that comprises: a barcode sequence, a primer binding sequence, and optionally a linker-spacer sequence between the barcode sequence and the primer binding sequence, as disclosed herein. The primer binding sequence may be any sequence to which a complementary primer can bind, which together with the barcode sequence allows for amplification of the barcode. In some embodiments, the primer binding sequence is conveniently a polyA sequence, which allows a gRNA to be captured alongside a cell's mRNA by reverse transcriptase when primed by an oligo-dT primer, for example during a single cell RNA-seq protocol. However, one of skill in the art will recognize that in any of the embodiments disclosed herein, a primer sequence other than the disclosed polyA sequence can be used.

Example 1

The experimental qPCR protocol used to generate the data in FIG. 4 was as follows.

Individual CRISPR gRNAs (T2-polyA, T2) were synthesized using the barcoding library prep protocol, packaged into virus, and used to infect 293T-Cas9 cells. After 7 days, the 293T cells were harvested and RNA was extracted using the Zymo ZR RNA Microprep kit. For both T2-polyA and T2, 3 first strand RT reactions were performed with NEB ProtoScript II Enzyme (following the standard protocol) and 150 ng input RNA.

i. polyT primer (supplied with the Protoscript II kit)
ii. Degenerate random hexamer (from IDT)
iii. polyT primer with no enzyme (the no RT control)

The RT product was diluted with 30 uL H₂O and 2 uL of the diluted product was used for qPCR, with 1 uL F primer, 1 uL R primer, 6 uL H20, and 10 uL 2× Kapa SYBR Fast Master mix. Both gRNA specific primers and GAPDH primers were used for the control. The gRNA specific primers were:

```
gRNA_qPCR_F_V2    GCTAGAAATAGCAAGTTAAAATAAGGC
                  (SEQ ID NO: 6)
gRNA_qPCR_R_V2    CGACTCGGTGCCACTTTTTC
                  (SEQ ID NO: 7)
```

Relative expression was calculated from Cq scores for gRNA to GAPDH quantification. The raw data is in the table below. The formula used was Relative Exparession=$2^{gRNAC_q - GAPDHC_q}$

TABLE 1

| Sample Name | RT Primer | gRNA Target Cq | GAPDH Target Cq |
|---|---|---|---|
| T2-polyA | polyT | 21.97 | 23.15 |
| T2-polyA | No RT | 27.74 | 26.36 |
| T2-polyA | Randomer | 22.86 | 20.02 |
| T2-noPolyA | polyT | 27.06 | 22.23 |
| T2-noPolyA | No RT | 28.86 | 31.09 |
| T2-noPolyA | Randomer | 22.5 | 18.93 |
| NTC | N/A | 29.02 | N/A |

The DropSeq library prep protocol was adapted with changes in the library prep section after the SMART PCR amplification. The PCR product was essentially split into cDNA and gRNA aliquots, standard tagmentation was performed on the cDNA aliquots and gRNA specific primers were used to amplify and attach Nextera adapters to the gRNA aliquot. FIG. 2 summarizes the procedure.

Figure 16:
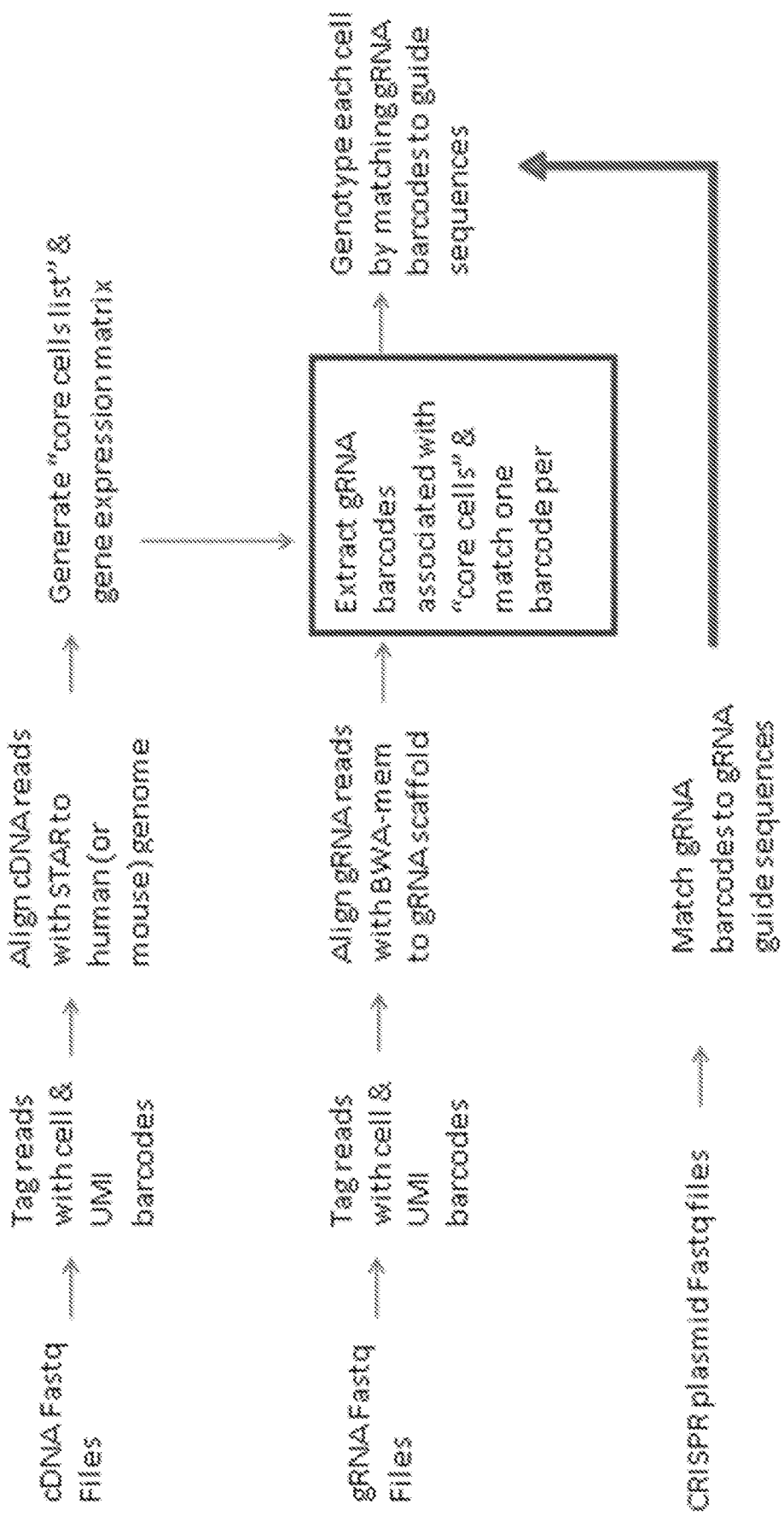
FIG. 16. An embodiment of an exemplary computational pipeline for genotyping the cells is provided.

The computational pipeline for genotyping the cells is provided in FIG. 16.

Figure 17:
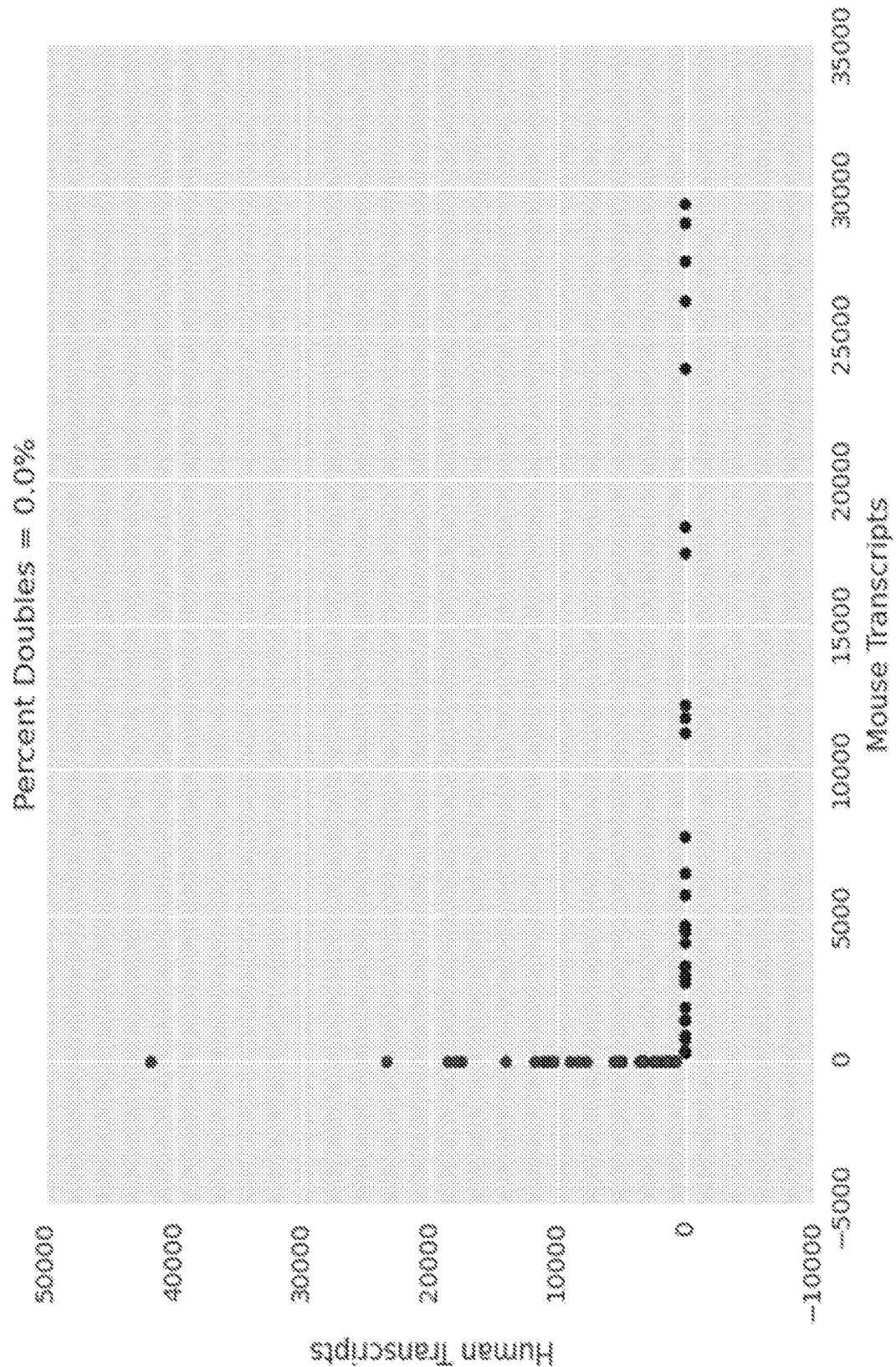
FIG. 17. An embodiment of doublet validation performed using the standard DropSeq protocol with a 50:50 mix of human and mouse iPSCs. The doublet plot is provided (the red dots ranging from 0 to about 4000 human transcripts correspond to human iPSCs and the blue dots ranging from 0 to about 30000 mouse transcripts correspond to mouse iPSCs).

Doublet validation was done using the standard DropSeq protocol with a 50:50 mix of human and mouse iPSCs. The doublet plot is provided in FIG. 17.

Example 2

Scalable Functional Screening by Sequencing and CRISPR-Cas9 Screening

We report the development and integration of two complementary methodologies, namely, high-throughput CRISPR-Cas9 screening, and single cell RNA-seq. We performed perturbations via CRISPR-interference and analyzed the resulting effect on gene expression using massive single-cell transcriptomic profiling (SEUSS). We validated our ability to link genotype to transcriptomic phenotype by demonstrating that the correct target gene was downregulated in the cells that received the corresponding gene knockdown.

Figure 18:
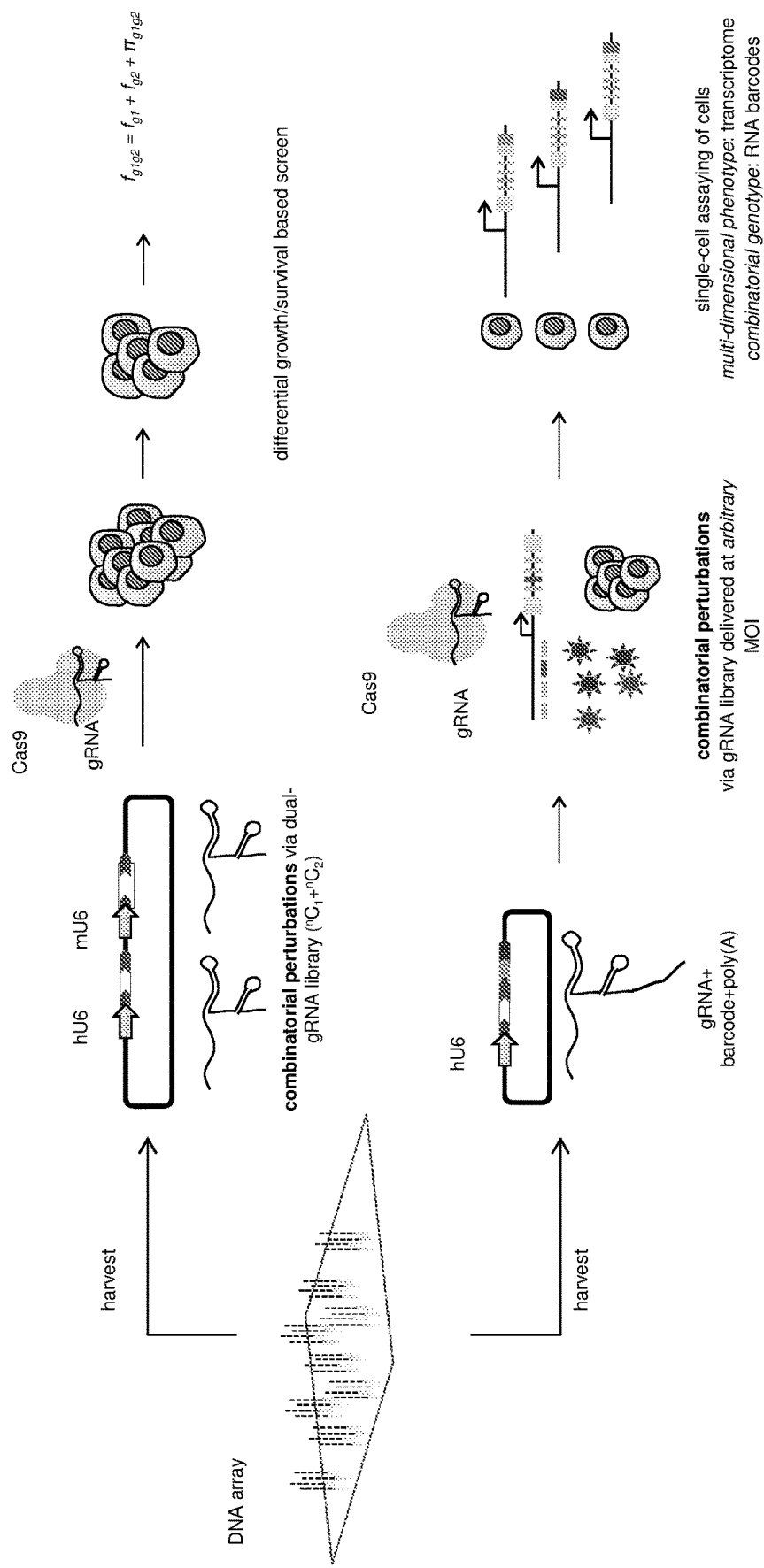
FIG. 18. An embodiment of Scalable functional Screening by Sequencing (SEUSS) to assay the transcriptomic effects of functional CRISPR-Cas9 perturbations.

Recently, the advent of droplet-based single-cell RNA sequencing has enabled us to assay the transcriptome of hundreds of thousands of individual cells. (Macosko E Z, et al. Cell. 2015 May 21; 161(5):1202-14; and Zheng G X, et al. Nat Commun. 2017 Jan. 16; 8:14049). To integrate high-throughput CRISPR-Cas9 screens and massively parallel single cell RNA-Seq, we developed a technique: ScalablE fUnctional Screening by Sequencing (SEUSS) to assay the transcriptomic effects of functional CRISPR-Cas9 perturbations (FIG. 18). SEUSS can be run in parallel alongside a traditional high-throughput CRISPR-Cas9 growth screen (FIG. 18).

Results

Figure 19:
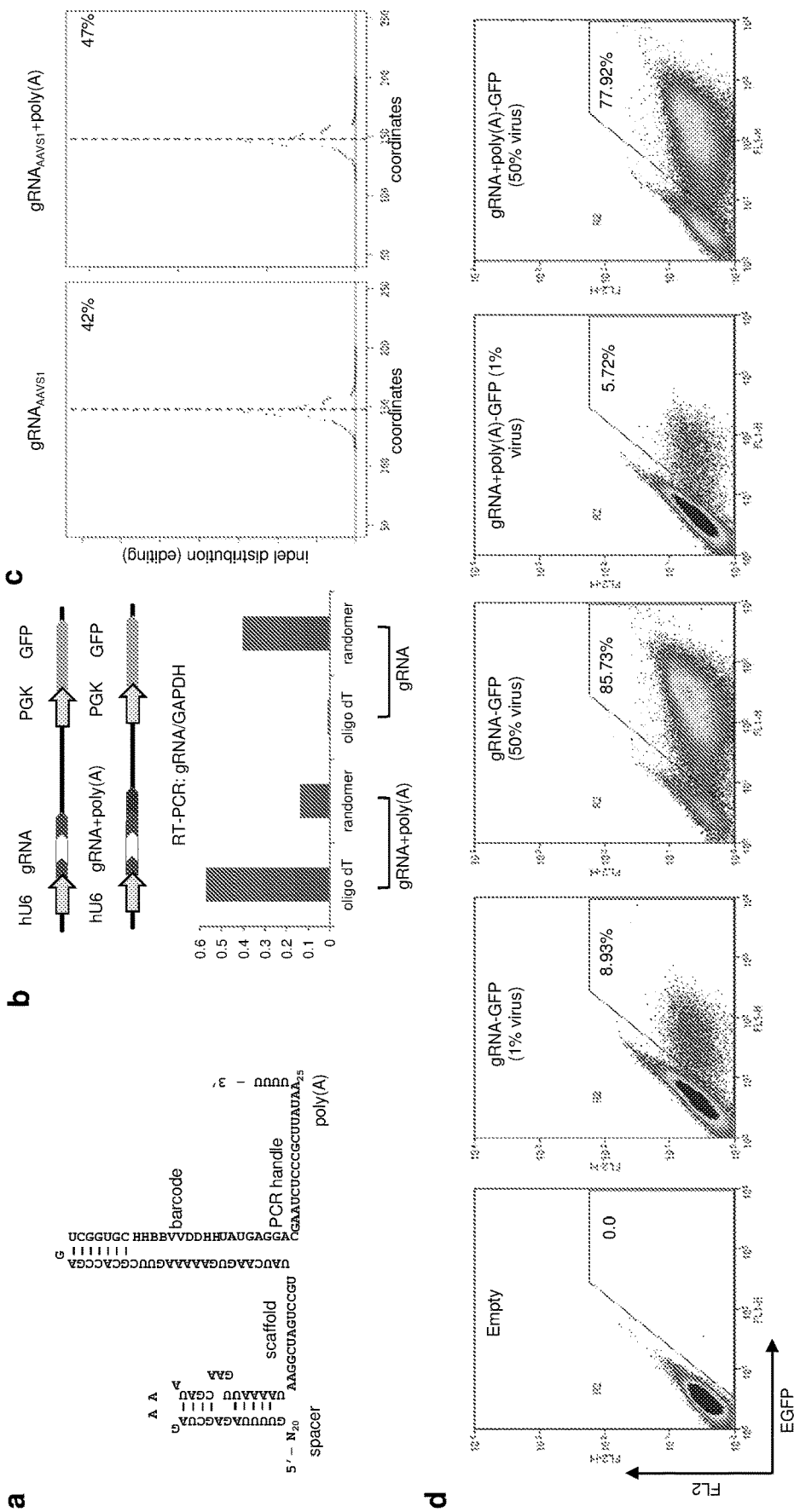
FIG. 19. An embodiment of confirmation of function of novel gRNA design and detection via RNA capture and sequencing approaches used in single-cell transcriptome sequencing. (a) an embodiment of an exemplary CRISPR-Cas9 construct bearing a spacer sequence, gRNA scaffold sequence, a 10 bp random "genotype" barcode, a 25 bp PCR handle, and a 25 bp poly(A) tail at the 3' end of the gRNA scaffold. The nucleotide sequence shown corresponds to SEQ ID NO: 2. The barcode sequence may be completely arbitrary. In some instances, a pattern in the barcode sequence may be chosen so that there is an underlying pattern to the barcode. For example, the barcode shown (HHBBVVDDHH) may have any nucleotide present at each position or there may be an underlying pattern. (b) in this embodiment, the poly(A) tail enabled detection of gRNAs after RT-PCR using oligo-d(T) capture probes. (c) in this embodiment, the poly(A) gRNA design retains similar functionality compared with the conventional design, as assayed by their ability to robustly introduce non-homologous end joining (NHEJ) mediated in-dels at the AAVS1 locus. (d) in this embodiment, presence of the poly(A) stretch did not compromise lentiviral titers, as equal amounts of virus from each production yielded comparable GFP signal from the downstream PGK-GFP cassette.

To link genetic modifications to transcriptome information in individual cells, we designed a novel CRISPR-Cas9 gRNA lentiviral library format, in which each gRNA bears a distinct RNA barcode and a 3' poly(A) sequence. Specifically, we fused a 12 bp random "genotype" barcode, a 25 bp PCR handle, and a 25 bp poly(A) tail at the 3' end of the gRNA scaffold (FIG. 19a). The term PCR handle, linker and linker-spacer are used interchangeably throughout this disclosure. To comprehensively validate this design we synthesized two lentiviral constructs, each bearing the same guide-RNA spacer sequence targeting the AAVS1 locus, but one based on the poly(A) tail architecture and the other based on the conventional gRNA scaffold. Each construct was also designed to include a downstream GFP cassette under the control of a PGK promoter. Each construct was packaged and stably delivered into 293T cells along with a Cas9 expressing lentivirus and assayed for functionality on multiple fronts: One, we confirmed that presence of the poly(A) tail enabled detection of gRNAs after RT-PCR when using oligo-d(T) capture probes (FIG. 19b). The droplet based single-cell assays utilize oligo-d(T) coated beads for transcriptome capture; two, the poly(A) gRNA design retained similar functionality vis-à-vis the conventional design as assayed by their ability to robustly introduce non-homologous end joining (NHEJ) mediated in-dels at the AAVS1 locus (FIG. 19c); and three, we confirmed that the presence of a poly(A) stretch did not compromise lentiviral titers, as equal amounts of virus from each production yielded comparable GFP signal from the downstream PGK-GFP cassette (FIG. 19d). Lentiviral constructs typically do not bear poly(A) signals. We demonstrated that he full-length RNA genome is efficiently transcribed during viral production. Taken together, we established that our novel gRNA design is functional and can be detected via standard RNA capture and sequencing approaches used in single-cell transcriptome sequencing.

Figure 20:
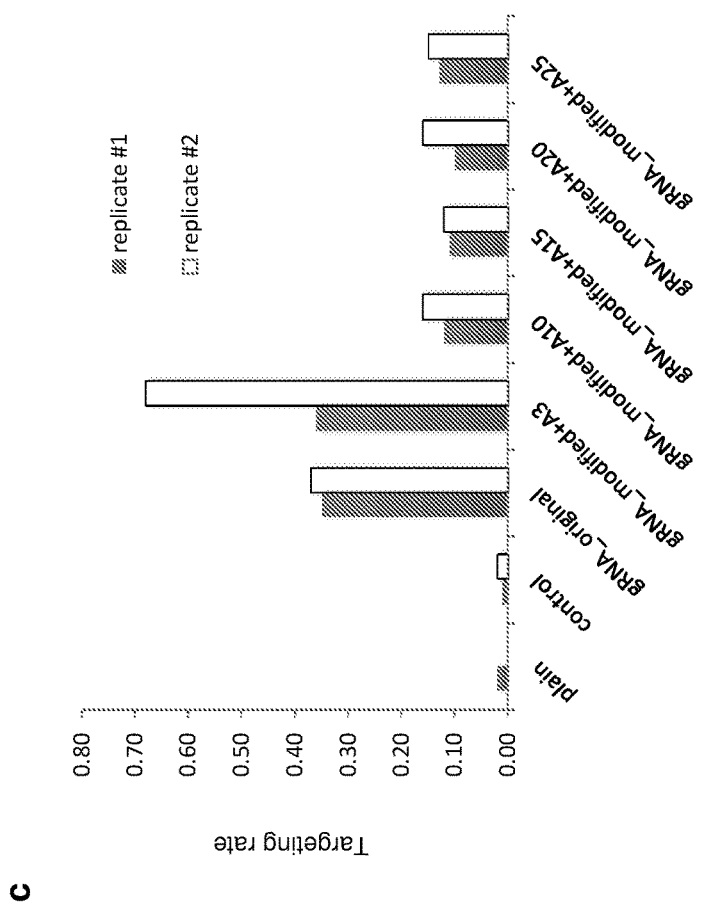
FIG. 20. An embodiment of an alternative gRNA designs in which the poly(A) is inserted in the hairpin structure of gRNA instead of appending to the tail (a) (SEQ ID NO: 3) and (b) (SEQ ID NO: 4). (c) Rates of genome editing (targeting rate) by the alternative gRNAs.
Figure 20:
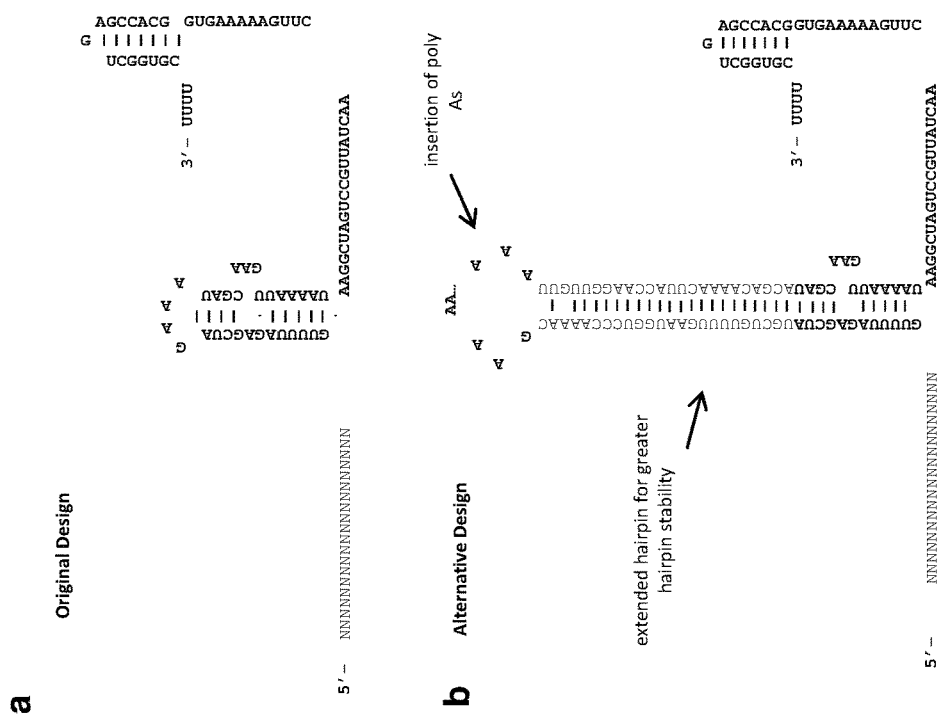

In addition, we developed an alternative gRNA design in which the poly(A) were inserted in the hairpin structure of gRNA instead of appending to the tail (FIGS. 20a and 20b). Modified gRNAs with various length of consecutive As and extended hairpin stem length showed significant genome editing, indicating that this gRNA design was also suitable for standard RNA capture and sequencing approaches.

Figure 21:
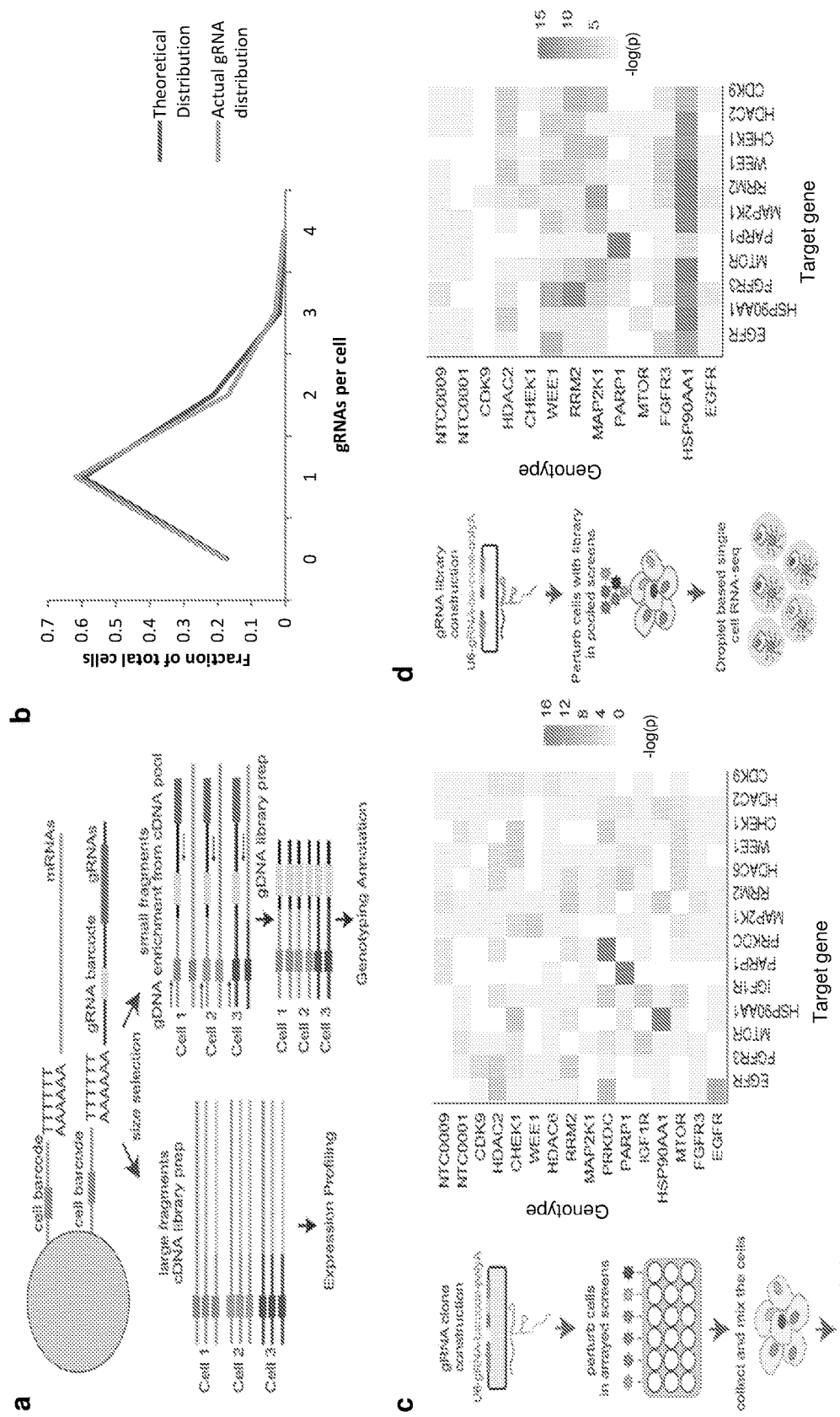
FIG. 21. An embodiment of functional analysis of 17 gRNAs containing a unique 12 bp barcode present between scaffold and polyA sequence. Together, the barcode, the linker-spacer and the polyA sequence constitute an RNA capture and sequencing domain for downstream genotyping. (a) Computational genotyping approach that confidently assigns a guide RNA (or multiple guide RNAs in the case where a cell receives more than one lentiviral vector) to each cell, thus linking the guide RNA to the cell's transcriptome. (b) distribution of guide RNAs per cell to a theoretical Poisson distribution (the guides were pooled into a single sample), (c) expression of genes targeted by the CRISPRi guide RNAs in both the single well validation experiment, (d) knockdown of HSP90AA1 and PARP1 by their respective gRNAs.

We cloned 17 gRNAs which showed the highest fitness effects in previous CRISPRi fitness screens, and three non-targeting gRNA controls. Each gRNA was designed with a unique 12 bp barcode present between scaffold and polyA sequence for downstream genotyping. We transduced KRAB-dCas9 HeLa cells with the twenty gRNA-polyA constructs in an array format to verify effects of the single gene perturbation (FIG. 21c) and in a pooled format (FIG. 21d). Our ability to run these screens in a pooled format where all the gRNA constructs are pooled in a single sample demonstrates transcriptome-wide scalability.

To enable multi-parameter phenotyping, single cells were collected at four days after transduction and were pooled together and run through the 10× genomics Chromium single cell RNA-seq system. Because our custom gRNA design contains a polyA tail, the gRNA was captured alongside the cell's mRNA during the single cell RNA-seq protocol. Note that our guide RNA will be picked up by any single-cell RNA-seq protocol that uses polyT primers, and is thus highly compatible with a wide array of single-cell RNA-seq technologies, including recent technologies such as Split-Seq (Rosenberg A B 2017 "Scaling single cell transcriptomics through split pool barcoding" BioRxiv. doi: on the internet at: doi.org/10.1101/105163).

After reverse transcription of the mRNA/gRNAs, we performed a PCR-based amplification of the gRNAs from the cDNA pool using the PCR handle incorporated 3' to the RNA barcode (FIG. 21a). Given the small size and polymerase III transcribed gRNAs, we found this enrichment step massively boost our ability to reliably establish each cell's genotype. The enriched gRNA library and the corresponding cDNA libraries were processed according to the scRNA-seq protocol, and sequenced on an Illumina HiSeq device.

To assign CRISPR-Cas9 perturbations to individual cells, we developed a computational genotyping approach that confidently assigns a guide RNA (or multiple guide RNAs in the case where a cell receives more than one lentiviral vector) to each cell, thus linking the guide RNA to the cell's transcriptome. (FIG. 21a). For our pooled experiment (where the guides were pooled into a single sample), we fit the distribution of guide RNAs per cell to a theoretical Poisson distribution (FIG. 21b). This serves as validation that our genotyping pipeline results in a sensible number of guide RNAs called per cell. Additionally, this illustrates that in a pooled experiment, we are able to assign gRNAs to over 80% of the cells.

To further validate our ability to link guide RNAs (genotype) to transcriptomic effects (phenotype), we looked at the expression of the genes targeted by the CRISPRi guide RNAs in both the single well validation experiment (FIG. 21c) and the pooled experiment (FIG. 21d). Because we are using CRISPR-interference, we expect downregulation of the target gene. For the single well validations, we can see that EGFR, HSP90AA1, PARP1, and PRKDC are clearly knocked down by their respective guide RNAs via the heatmap (FIG. 21c). The smaller the p-value (the darker the heatmap square), the more significant the knockdown. The pooled experiment is significantly noisier, but we can still see a clear knockdown of HSP90AA1 and PARP1 by their respective gRNAs (FIG. 21d).

Figure 22:
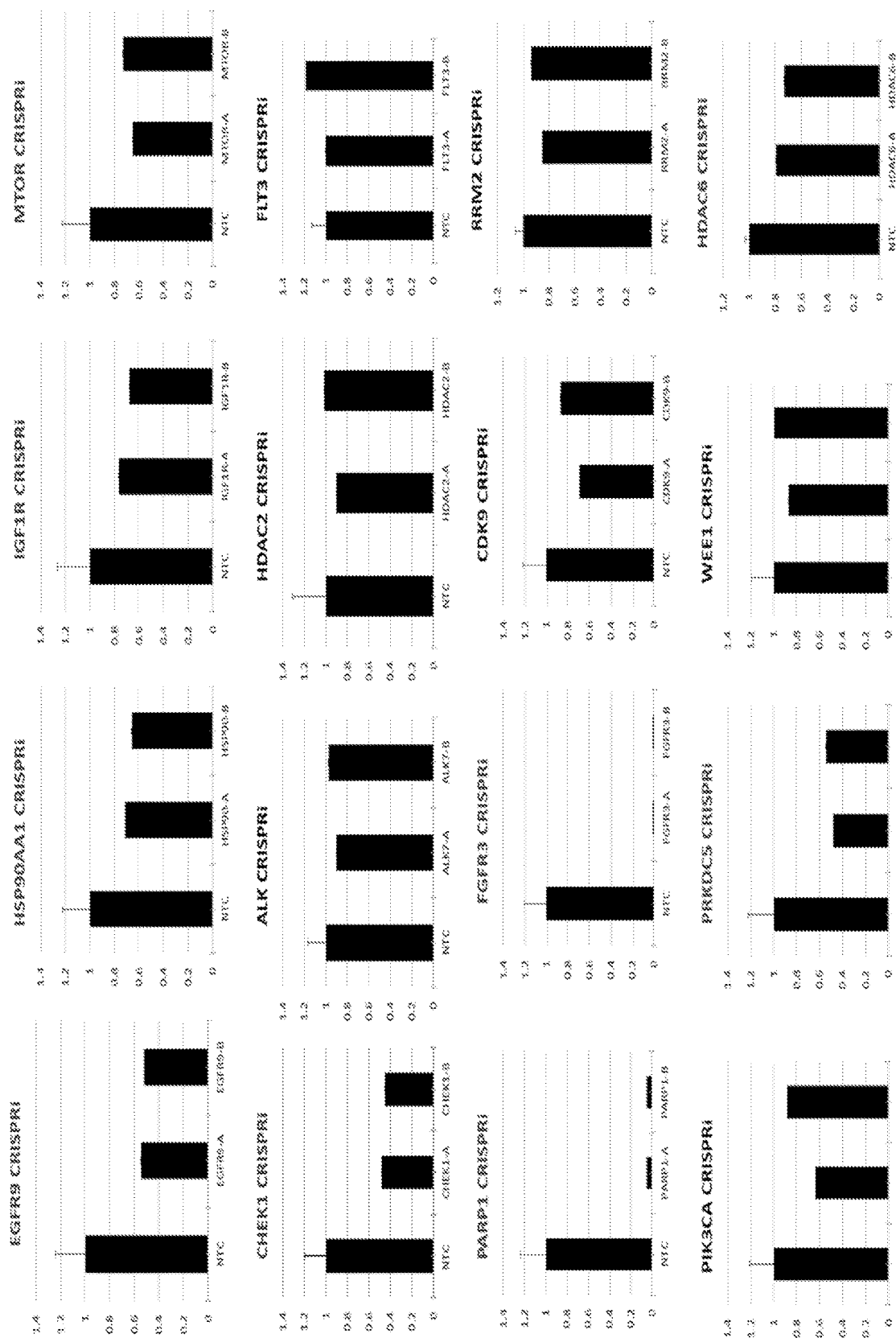
FIG. 22. An embodiment of qPCR of the target genes on individual well CRISPRi knockdowns.

As additional validation for the target gene knockdowns, we performed qPCR of the target genes on individual well CRISPRi knockdowns (FIG. 22). As expected, all of the genes detected as knocked down in our single-cell RNA-seq data were also knocked down in the qPCR data. Some of the genes that were shown to be knocked-down in qPCR data were not called as knocked-down in the single-cell RNA-seq. This may be a limitation of the single-cell RNA-Seq method's inability to detect lowly expressed genes.

Methods

A. Design and Clone of gRNA Constructs

A panel of 17 cancer relevant genes were selected for study. The gRNAs were previously verified in a pooled CRISPR-based functional screens. Three gRNAs were designed to be "non-targeters" that should not target any specific site in the genome. The oligonucleotide were ordered from Integrated DNA Technologies, annealed to generate double strands DNA. To attach the 12 bp random barcode to each gRNA, the second step PCR were performed for 6 cycles using the following primers:

```
OLS_gRNA-SP_F:
                                        (SEQ ID NO: 8)
TATATATCTTGTGGAAAGGACGAAACACCG

OLS_gRNA-SP_12mer_R:
                                        (SEQ ID NO: 9)
TATAAGCGGGAGATTCGTCCTCATANNNNNNNNNNNNGCACCGACTCGGT

GCCACTTTTTCAAGTTGATAACGGACTAGCCTTATTTTAACTTGCTATTT

CTAGCTCTAAAAC
```

Amplicons were then purified and further treated with Exonuclease I to remove excess primers. The 169 bp amplicons were separated in 2% agarose gel electrophoresis and purified by QIAquick gel extraction kit. Subsequently, 4 μg of LV-gRNA-polyA vector was digested by 3 μl AgeI (NEB) in a 50 μl reaction at 37° C. for 3 hours. After digestion, the vector was treated with 2 μl of Calf Intestinal Alkaline Phosphatase (NEB) at 37° C. for 30 minutes, then purified by QIAquick PCR Purification Kit (QIAGEN). We assembled 200 ng linearized LV-gRNA-polyA vector with 36 ng (molar ratio 1:10) barcoded gRNA inserts in a 20 μl Gibson assembly reaction at 50° C. for 1 hour and performed ten reactions to obtain a high yield. The product was pooled and purified by QIAquick PCR Purification Kit (QIAGEN) and then transformed into One Shot Stb13 Chemically Competent *E. coli* (Invitrogen). Single clones were picked and sequenced.

The gRNA sequences and corresponding barcodes for the clones we used in this study were as follows:

| Gene | Spacers | SEQ ID NO | Barcodes | SEQ ID NO |
|---|---|---|---|---|
| FGFR3 | GCCCGTGCGGGCAGAGGCGT | 10 | ATCAGACCCATC | 11 |
| WEE1 | GCTCATCGCGGCCCTGGGGA | 12 | GCGCAGGTAGAG | 13 |
| MTOR | GTCCTCTAAGCCGGGAGCGA | 14 | TCGACTCACTCA | 15 |
| RRM2 | GTGATGGGCGCGAGCGGGACA | 16 | ACGACTACTCGC | 17 |
| PRKDC | GTGTGCGTTGCTCCCTGCTG | 18 | TAGATCAAACCC | 19 |
| IGF1R | GCCGGCGAGGGGCAGAAACG | 20 | ACGCACTCCGTG | 21 |
| HDAC6 | GAAACGCTAGGGGCGGGATC | 22 | TGAACATCGATC | 23 |
| FLT3 | GCGAGGCGCGCCGCTCCAGG | 24 | CTGAGTTTATTC | 25 |
| CDK9 | GCAGCAGCGACTGGGGGCGG | 26 | TAAAATATACTA | 27 |
| CHEK1 | GAGGATATAGGGAGCGGTAT | 28 | TCGACGATATGC | 29 |
| ALK | GACCCTCCGAACAGAGGCGG | 30 | TTGAGGCACCAA | 31 |
| HSP90AA1 | GGCGCGCGCAGGCCCTGCTCG | 32 | ATTACTGATACA | 33 |
| PARP1 | GCGTGCGCTCACCCAGCCGC | 34 | CTAGAATCTCGT | 35 |
| HDAC2 | GATAGTCCCGCGGGAAGGGC | 36 | CGTCAGATATAA | 37 |
| MAP2K1 | GGAAAGCGCCGCATCCCGGG | 38 | GAGAGAGAAAAA | 39 |
| EGFR | GCTGCCCCGGCCGTCCCGGA | 40 | AGCCTACCGTGT | 41 |
| PIK3CA | GGGAGTCTCCGGCACCCACC | 42 | TTACGCAATCAC | 43 |
| NTC0001 | ACGGAGGCTAAGCGTCGCAA | 44 | AAGTCTTGCTAG | 45 |
| NTC0006 | TACTAACGCCGCTCCTACAG | 46 | CCCCATAAATAG | 47 |
| NTC0009 | TAGACAACCGCGGAGAATGC | 48 | AGCTATTGGTGC | 49 |

B. Cell Culture and Pooled Screen

HEK293T cells were maintained in DMEM medium supplemented with 10% fetal bovine serum. To produce lentivirus, HEK293T cells were seeded in 15 cm tissue culture dishes one day before transfection so that they were 70-80% confluent at the time of transfection. Prior to transfection, culture media was changed to pre-warmed DMEM medium supplemented with 10% fetal bovine serum. For each 15 cm dish, 36 µl of Lipofectamine 3000 (Life Technologies) was diluted in 1.2 ml OptiMEM (Life Technologies). Separately, 3 µg of pMD2.G (Addgene #12259), 12 µg of pCMV delta R8.2 (Addgene #12263), 9 µg of lentiviral vector and 48 µl of P3000 Reagent were diluted in 1.2 ml OptiMEM. After incubation for 5 min, the Lipofectamine 3000 mixture and DNA mixture were combined and incubated at room temperature for 30 min. The mixture was then added to HEK293T cells dropwise. Viral particles were harvested 48 hours and 72 hours after transfection, further concentrated using Centricon Plus-20 centrifugal ultrafilters with a cutoff 100,000 NMWL (Millipore) to a final volume of 450 µl, and then aliquoted and frozen at −80° C.

The stable human cell lines HeLa in which the KRAB-dCas9 is stably integrated into the human AAVS1 site, were used for screening assays. Cells were expanded and frozen in multiple aliquots so that subsequent experiments could be performed with low (<5) passage number. These were grown in DMEM supplemented with 10% fetal bovine serum and blasticidin S (10 µg/ml). After transduction with library, the cells were selected with 5 µg/ml puromycin selection. Nearly 100% killing was observed in plain cells with these doses after 120 hours of exposure.

The pooled library of gRNA-barcode-polyA constructs was packaged into lentiviruses with Hela cell line infected at MOI=2 to ensure that most cell had two gRNA-barcode-polyA constructs. Puromycin selection was started 2 days after transduction and the cells were dissociated into single cells for droplet based single cells RNA sequencing at day 4.

Single Cells RNA-Seq Library Preparation

Two methods, drop-seq (Macosko E Z, et al. Cell. 2015 May 21; 161(5):1202-14) and 10x genomics (Zheng G X, et al. Nat Commun. 2017 Jan. 16; 8:14049) were used to capture single cells for RNA-seq according to their respective protocols. Around 2000 cells were captured in each Drop-seq run and 10,000 cells were captured in each 10x genomics run. The cDNA library were prepared as the standard protocol, and barcoded gRNAs were enriched from the cDNA pool by PCR first and then were attached with Illumina adaptors and indexes. The long fragments of cDNA products were size selected using SPRI beads at 0.55× ratio and the supernatant were saved for a further selection at 1:1.6 ratio to preserve the small fragments. The small fragments of cDNA library were used as template for gRNA enrichment PCR. The thermocycling parameters were: 95° C. for 30 s, 18 cycles of (98° C. for 15 s, 65° C. for 15 s, 72° C. for 30 s), and 72° C. for 5 min. For coupling with Drop-seq method, the primers were as follows:

```
P5-TSO-hybrid (the same one as drop-seq protocol):
                                        (SEQ ID NO: 50)
AATGATACGGCGACCACCGAGATCTACACGCCTGTCCGCGGAAGCAGTGG TATCAACGCAGAGT*A*C
Asterisk refers to phosphorothioate bond.

gRNA_Enrichment_F:
                                        (SEQ ID NO: 51)
GTCTCGTGGGCTCGGAGATGTGTATAAGAGACAGAGCAAGTTAAAATAAG

GCTAGTCCG.
```

For 10x genomics runs, the primers were as follows:

```
P5:
                                        (SEQ ID NO: 52)
AATGATACGGCGACCACCGA gRNA_Enrichment_F:
                                        (SEQ ID NO: 53)
GTCTCGTGGGCTCGGAGATGTGTATAAGAGACAGAGCAAGTTAAAATAAG

GCTAGTCCG.
```

The amplicons were purified using AMPure XP beads at 1:1.2 ratio. Then 10 ng of enriched gRNA-barcode were further amplified in step 2 PCR for 6 cycles to attach with Illumina adaptors and indexes, using P5-TSO-hybrid or P5 primers (for Drop-seq and 10x genomics methods, respectively) and Nextera N70x primers.

The cDNA libraries and gRNA libraries was quantified by real-time PCR using Illumina Library Quantification (Kapa Biosystems) and used for downstream sequencing on the Illumina HiSeq Rapid run platform.

Computational Analysis

This pipeline uses the software from DropSeq or 10× genomics to generate the UMI matrix.

Starting with cDNA Fastq Files:
1. Cell and Molecule tags are extracted
2. cDNA reads are aligned to the human hg19 genome via STAR
3. UMI count matrix generated from cDNA reads Starting with gRNA Fastq Files:
1. Cell and Molecule tags are extracted
2. gRNA reads are aligned to the gRNA scaffold via BWA
3. gRNA barcodes are extracted by looking for the flanking sequences before and after the 12 bp barcode. The flanking sequences are allowed to have a 1 bp mismatch. Barcodes are considered valid if they are at least 11 bp long, and they can have at most 1 base with a sequencing quality of less than 20.

Matching gRNA Reads to Cells in the UMI Count Matrix and Genotyping the Cells
1. The cell barcodes in the gRNA reads are matched to the cell barcodes in the UMI count matrix, allowing for a 1 edit distance difference
   a. If a gRNA cell tag matches multiple cell tags in the UMI count matrix (this happens because we allow for 1 edit distance mismatches), the read is discarded
2. For each cell in the UMI matrix, the number of reads for each gRNA barcode is counted, and gRNA barcodes are collapsed with edit distance 1 and the respective read counts summed. We also sum the respective UMI counts for each gRNA barcode.
3. gRNA barcodes that have less than 10% of total reads in the cell, or 10% of total UMIs in the given cell are discarded. This step removes most of the "noise" present in the gRNA reads.
4. After a gRNA barcode (or barcodes) is assigned, we look in the barcode to spacer plasmid library for that barcode, again allowing for a 1 edit distance mismatch to assign a gRNA identity (or identities) to each cell.

Target Gene Knockdown Validation

The UMI counts matrix is assembled and unwanted sources of variation (library size, mitochondrial fraction, and single cell processing batch) are regressed away using negative binomial regression via the Seurat package. The target genes are tested for downregulation by first ranking each cell according to its normalized expression of a given target gene, and then testing each genotype to see if it contained cells with an abnormally large amount of low rankings.

The person skilled in the art realizes that the present disclosure by no means is limited to the embodiments described above. On the contrary, many modifications and variations are possible within the scope of the appended claims.

Additionally, variations to the disclosed embodiments can be understood and effected by the skilled person in practicing the claimed disclosure, from a study of the drawings, the disclosure, and the appended claims. In the claims, the word "comprising" does not exclude other elements or steps, and the indefinite article "a" or "an" does not exclude a plurality. The mere fact that certain features are recited in mutually different dependent claims does not indicate that a combination of these features cannot be used to advantage. Also two or more steps or processes may be performed concurrently or with partial concurrence. Further, in some embodiments, the steps or processes of the methods may be performed in an order different from what has been disclosed. All such variations are within the scope of the disclosure. Additionally, even though the disclosure has been described with reference to specific exemplifying embodiments thereof, many different alterations, modifications and the like will become apparent for those skilled in the art. Any suitable combination of the elements and acts of the various embodiments described above can be combined to provide further embodiments. The accompanying claims and their equivalents are intended to cover such forms or modifications as would fall within the scope and spirit of the disclosure.

While the present description has been provided in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference for the disclosures referenced herein and in their entirety.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. In some embodiments, components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

What is claimed is:

1. A guide RNA comprising from 5' to 3':
 (a) a gRNA spacer sequence at the 5' end of the guide RNA, wherein the spacer sequence is complementary to a target gene,
 (b) a scaffold sequence that binds to Cas9, and
 (c) an RNA capture and sequencing domain comprising:
  (1) a barcode sequence of 7-20 nucleotides, and
  (2) a primer binding sequence comprising a polyA sequence of 20-25 adenosines.

2. The guide RNA of claim 1, wherein said barcode sequence is uniquely associated with said gRNA spacer sequence.

3. The guide RNA of claim 1, wherein a linker sequence is positioned between said barcode sequence and said primer binding sequence.

4. The guide RNA of claim 1, wherein the barcode sequence is a patterned sequence.

5. A nucleic acid encoding the guide RNA of claim 1.

6. A vector comprising the nucleic acid of claim 5.

7. A cell expressing the guide RNA of claim 1.

8. The cell of claim 7, wherein said cell further expresses a Cas9 polypeptide.

9. A library comprising a plurality of guide RNAs of claim 1.

10. The library of claim 9, wherein said library comprises at least 100 distinct guide RNAs of claim 1.

11. The library of claim 9, wherein said plurality of guide RNAs comprises at least 1000 guide RNAs.

12. The library of claim 9, wherein said plurality of guide RNAs comprises at least 10000 guide RNAs.

13. The library of claim 9 wherein said plurality of guide RNAs are cloned into a viral vector.

14. The library of claim 13, wherein said viral vector is a lentiviral vector.

15. A method of introducing a genetic perturbation into a cell comprising:
 contacting a target nucleic acid in said cell with a guide RNA of claim 1 and a Cas9 nuclease; and performing a guide RNA-mediated genetic modification process to introduce said genetic perturbation into said cell.

16. The method of claim 15, wherein said guide RNA-mediated genetic modification process comprises a CRISPR genetic modification process.

17. A method of assessing an effect of at least one genetic perturbation on RNA expression in a cell comprising:
 performing an RNA expression analysis on a cell in which at least one genetic perturbation has been introduced using a guide RNA of claim 1,
 measuring a change in RNA expression of at least one gene, and
 identifying the at least one genetic perturbation that is responsible for said change in RNA expression of at least one gene by determining the sequence of said barcode in said guide RNA.

18. The method of claim 17, wherein said RNA expression analysis comprises a single cell RNA expression analysis.

19. The method of claim 17, wherein said at least one genetic perturbation has been introduced by transducing said cell with a virus encoding said guide RNA.

* * * * *

SEQUENCE LISTING

<160> NUMBER OF SEQ ID NOS: 53

<210> SEQ ID NO 1
<211> LENGTH: 183
<212> TYPE: RNA
<213> ORGANISM: Artificial Sequence
<220> FEATURE:

```
<223> OTHER INFORMATION: synthetic construct
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (43)..(43)
<223> OTHER INFORMATION: n is a, c, g, or u
<220> FEATURE:
<221> NAME/KEY: misc_feature
<222> LOCATION: (49)..(49)
<223> OTHER INFORMATION: n is a, c, g, or u
<220> FEATURE:
<221> NAME/KEY: variation
<222> LOCATION: (55)..(55)
<223> OTHER INFORMATION: y is u or c
<220> FEATURE:
<221> NAME/KEY: variation
<222> LOCATION: (56)..(56)
<223> OTHER INFORMATION: w is a or u
<220> FEATURE:
<221> NAME/KEY: variation
<222> LOCATION: (57)..(57)
<223> OTHER INFORMATION: r is g or a
<220> FEATURE:
<221> NAME/KEY: misc_feature
<222> LOCATION: (120)..(129)
<223> OTHER INFORMATION: n is a, c, g, or u

<400> SEQUENCE: 1
nnnnnnnnnn nnnnnnnnnn guuucagagc uaugcuggaa agnuywranc uaaacagcau      60
agcaaguuga aauaaggcua guccguuauc aagugaaaaa guucgcaccg agucggugcn     120
nnnnnnnnnu augaggacga aucucccgcu uauaaaaaaa aaaaaaaaaa aaaaaaaau     180 uuu                                                                  183

<210> SEQ ID NO 2
<211> LENGTH: 161
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (98)..(107)
<223> OTHER INFORMATION: n is a, c, g, or u

<400> SEQUENCE: 2
nnnnnnnnnn nnnnnnnnnn guuuuagagc uagaaauagc aaguuaaaau aaggcuaguc      60
cguuaucaaa gugaaaaagu ucgcaccgag ucggugcnnn nnnnnnuau gaggacgaau     120 cucccgcuua uaaaaaaaaa aaaaaaaaa aaaaaauuu u                          161

<210> SEQ ID NO 3
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: n is a, c, g, or u

<400> SEQUENCE: 3
nnnnnnnnnn nnnnnnnnnn guuuuagagc uagaaauagc aaguuaaaau aaggcuaguc      60
```
cguuaucaac uugaaaaagu ggcaccgagu cggugcuuuu          100

<210> SEQ ID NO 4
<211> LENGTH: 152
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: n is a, c, g, or u

<400> SEQUENCE: 4
nnnnnnnnnn nnnnnnnnnn guuuuagagc uaugcuguuu ugaauggucc caaaacgaaa          60
aaaauuguug gaaccauuca aaacagcaua gcaaguuaaa auaaggcuag uccguuauca         120
acuugaaaaa guggcaccga gucggugcuu uu          152

<210> SEQ ID NO 5
<211> LENGTH: 174
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(21)
<223> OTHER INFORMATION: n is a, c, g, or t
<220> FEATURE:
<221> NAME/KEY: misc_feature
<222> LOCATION: (36)..(55)
<223> OTHER INFORMATION: n is a, c, g, or t
<220> FEATURE:
<221> NAME/KEY: misc_feature
<222> LOCATION: (99)..(118)
<223> OTHER INFORMATION: n is a, c, g, or t
<220> FEATURE:
<221> NAME/KEY: misc_feature
<222> LOCATION: (149)..(168)
<223> OTHER INFORMATION: n is a, c, g, or t

<400> SEQUENCE: 5
gnnnnnnnnn nnnnnnnnnn ngtttgagag ctaggnnnnn nnnnnnnnnn nnnnncctag          60
caagttcaaa taaggctagt ccgttctcaa cttggccann nnnnnnnnnn nnnnnnnnct         120
gcagggccaa gtggcaccga gtcggtgcnn nnnnnnnnnn nnnnnnnntt tttt          174

<210> SEQ ID NO 6
<211> LENGTH: 27
<212> TYPE: DNA
<213> ORGANISM: Artificial Sequence
<220> FEATURE:
<223> OTHER INFORMATION: Synthetic construct

<400> SEQUENCE: 6
gctagaaata gcaagttaaa ataaggc          27

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
cgactcggtg ccactttttc          20

<210> SEQ ID NO 8
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 8
tatatatctt gtggaaagga cgaaacaccg                                30

<210> SEQ ID NO 9
<211> LENGTH: 113
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (26)..(37)
<223> OTHER INFORMATION: n is a, c, g, or t

<400> SEQUENCE: 9
tataagcggg agattcgtcc tcatannnnn nnnnnnngca ccgactcggt gccacttttt    60
caagttgata acggactagc cttattttaa cttgctattt ctagctctaa aac          113

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
gcccgtgcgg gcagaggcgt                                            20

<210> SEQ ID NO 11
<211> LENGTH: 12
<212> TYPE: DNA
<213> ORGANISM: Artificial Sequence
<220> FEATURE:
<223> OTHER INFORMATION: synthetic construct

<400> SEQUENCE: 11
atcagaccca tc                                                    12

<210> SEQ ID NO 12
<211> LENGTH: 20
<212> TYPE: DNA
<213> ORGANISM: Artificial Sequence
<220> FEATURE:
<223> OTHER INFORMATION: synthetic construct

<400> SEQUENCE: 12
gctcatcgcg gccctgggga                                            20

<210> SEQ ID NO 13
<211> LENGTH: 12
<212> TYPE: DNA
<213> ORGANISM: Artificial Sequence
<220> FEATURE:
<223> OTHER INFORMATION: synthetic construct

<400> SEQUENCE: 13
gcgcaggtag ag                                                    12

```
<210> SEQ ID NO 14
<211> LENGTH: 20
<212> TYPE: DNA
<213> ORGANISM: Artificial sequence
<220> FEATURE:
<223> OTHER INFORMATION: synthetic construct

<400> SEQUENCE: 14
gtcctctaag ccgggagcga                                               20

<210> SEQ ID NO 15
<211> LENGTH: 12
<212> TYPE: DNA
<213> ORGANISM: Artificial sequence
<220> FEATURE:
<223> OTHER INFORMATION: synthetic construct

<400> SEQUENCE: 15
tcgactcact ca                                                       12

<210> SEQ ID NO 16
<211> LENGTH: 21
<212> TYPE: DNA
<213> ORGANISM: Artificial Sequence
<220> FEATURE:
<223> OTHER INFORMATION: synthetic construct

<400> SEQUENCE: 16
gtgatgggcg cgagcgggac a                                             21

<210> SEQ ID NO 17
<211> LENGTH: 12
<212> TYPE: DNA
<213> ORGANISM: Artificial Sequence
<220> FEATURE:
<223> OTHER INFORMATION: synthetic construct

<400> SEQUENCE: 17
acgactactc gc                                                       12

<210> SEQ ID NO 18
<211> LENGTH: 20
<212> TYPE: DNA
<213> ORGANISM: Artificial Sequence
<220> FEATURE:
<223> OTHER INFORMATION: synthetic construct

<400> SEQUENCE: 18
gtgtgcgttg ctccctgctg                                               20

<210> SEQ ID NO 19
<211> LENGTH: 12
<212> TYPE: DNA
<213> ORGANISM: Artificial Sequence
<220> FEATURE:
<223> OTHER INFORMATION: synthetic construct

<400> SEQUENCE: 19
tagatcaaac cc                                                       12

<210> SEQ ID NO 20
<211> LENGTH: 20
<212> TYPE: DNA
<213> ORGANISM: Artificial Sequence
<220> FEATURE:
<223> OTHER INFORMATION: synthetic construct
```

<400> SEQUENCE: 20
gccggcgagg ggcagaaacg                                              20

<210> SEQ ID NO 21
<211> LENGTH: 12
<212> TYPE: DNA
<213> ORGANISM: Artificial Sequence
<220> FEATURE:
<223> OTHER INFORMATION: synthetic construct

<400> SEQUENCE: 21
acgcactccg tg                                                      12

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
gaaacgctag gggcgggatc                                              20

<210> SEQ ID NO 23
<211> LENGTH: 12
<212> TYPE: DNA
<213> ORGANISM: Artificial Sequence
<220> FEATURE:
<223> OTHER INFORMATION: synthetic construct

<400> SEQUENCE: 23
tgaacatcga tc                                                      12

<210> SEQ ID NO 24
<211> LENGTH: 20
<212> TYPE: DNA
<213> ORGANISM: Artificial Sequence
<220> FEATURE:
<223> OTHER INFORMATION: synthetic construct

<400> SEQUENCE: 24
gcgaggcgcg ccgctccagg                                              20

<210> SEQ ID NO 25
<211> LENGTH: 12
<212> TYPE: DNA
<213> ORGANISM: Artificial Sequence
<220> FEATURE:
<223> OTHER INFORMATION: synthetic construct

<400> SEQUENCE: 25
ctgagtttat tc                                                      12

<210> SEQ ID NO 26
<211> LENGTH: 20
<212> TYPE: DNA
<213> ORGANISM: Artificial Sequence
<220> FEATURE:
<223> OTHER INFORMATION: synthetic construct

<400> SEQUENCE: 26
gcagcagcga ctggggcgg                                               20

<210> SEQ ID NO 27
<211> LENGTH: 12

<212> TYPE: DNA
<213> ORGANISM: Artificial Sequence
<220> FEATURE:
<223> OTHER INFORMATION: synthetic construct

<400> SEQUENCE: 27
taaaatatac ta                                              12

<210> SEQ ID NO 28
<211> LENGTH: 20
<212> TYPE: DNA
<213> ORGANISM: Artificial Sequence
<220> FEATURE:
<223> OTHER INFORMATION: synthetic construct

<400> SEQUENCE: 28
gaggatatag ggagcggtat                                      20

<210> SEQ ID NO 29
<211> LENGTH: 12
<212> TYPE: DNA
<213> ORGANISM: Artificial Sequence
<220> FEATURE:
<223> OTHER INFORMATION: synthetic construct

<400> SEQUENCE: 29
tcgacgatat gc                                              12

<210> SEQ ID NO 30
<211> LENGTH: 20
<212> TYPE: DNA
<213> ORGANISM: Artificial Sequence
<220> FEATURE:
<223> OTHER INFORMATION: synthetic construct

<400> SEQUENCE: 30
gaccctccga acagaggcgg                                      20

<210> SEQ ID NO 31
<211> LENGTH: 12
<212> TYPE: DNA
<213> ORGANISM: Artificial Sequence
<220> FEATURE:
<223> OTHER INFORMATION: synthetic construct

<400> SEQUENCE: 31
ttgaggcacc aa                                              12

<210> SEQ ID NO 32
<211> LENGTH: 21
<212> TYPE: DNA
<213> ORGANISM: Artificial Sequence
<220> FEATURE:
<223> OTHER INFORMATION: synthetic construct

<400> SEQUENCE: 32
ggcgcgcgca ggccctgctc g                                    21

<210> SEQ ID NO 33
<211> LENGTH: 12
<212> TYPE: DNA
<213> ORGANISM: Artificial Sequence
<220> FEATURE:
<223> OTHER INFORMATION: synthetic construct

<400> SEQUENCE: 33

```
attactgata ca                                                    12

<210> SEQ ID NO 34
<211> LENGTH: 20
<212> TYPE: DNA
<213> ORGANISM: Artificial Sequence
<220> FEATURE:
<223> OTHER INFORMATION: synthetic construct

<400> SEQUENCE: 34
gcgtgcgctc acccagccgc                                            20

<210> SEQ ID NO 35
<211> LENGTH: 12
<212> TYPE: DNA
<213> ORGANISM: Artificial Sequence
<220> FEATURE:
<223> OTHER INFORMATION: synthetic construct

<400> SEQUENCE: 35
ctagaatctc gt                                                    12

<210> SEQ ID NO 36
<211> LENGTH: 21
<212> TYPE: DNA
<213> ORGANISM: Artificial Sequence
<220> FEATURE:
<223> OTHER INFORMATION: synthetic construct

<400> SEQUENCE: 36
gatagtcccg cggggaaggg c                                          21

<210> SEQ ID NO 37
<211> LENGTH: 12
<212> TYPE: DNA
<213> ORGANISM: Artificial Sequence
<220> FEATURE:
<223> OTHER INFORMATION: synthetic construct

<400> SEQUENCE: 37
cgtcagatat aa                                                    12

<210> SEQ ID NO 38
<211> LENGTH: 20
<212> TYPE: DNA
<213> ORGANISM: Artificial Sequence
<220> FEATURE:
<223> OTHER INFORMATION: synthetic construct

<400> SEQUENCE: 38
ggaaagcgcc gcatcccggg                                            20

<210> SEQ ID NO 39
<211> LENGTH: 12
<212> TYPE: DNA
<213> ORGANISM: Artificial Sequence
<220> FEATURE:
<223> OTHER INFORMATION: synthetic construct

<400> SEQUENCE: 39
gagagagaaa aa                                                    12

<210> SEQ ID NO 40
<211> LENGTH: 20
<212> TYPE: DNA
<213> ORGANISM: Artificial Sequence
```

```
<220> FEATURE:
<223> OTHER INFORMATION: synthetic construct

<400> SEQUENCE: 40
gctgccccgg ccgtcccgga                                              20

<210> SEQ ID NO 41
<211> LENGTH: 12
<212> TYPE: DNA
<213> ORGANISM: Artificial Sequence
<220> FEATURE:
<223> OTHER INFORMATION: synthetic construct

<400> SEQUENCE: 41
agcctaccgt gt                                                      12

<210> SEQ ID NO 42
<211> LENGTH: 20
<212> TYPE: DNA
<213> ORGANISM: Artificial Sequence
<220> FEATURE:
<223> OTHER INFORMATION: synthetic construct

<400> SEQUENCE: 42
gggagtctcc ggcacccacc                                              20

<210> SEQ ID NO 43
<211> LENGTH: 12
<212> TYPE: DNA
<213> ORGANISM: Artificial Sequence
<220> FEATURE:
<223> OTHER INFORMATION: synthetic construct

<400> SEQUENCE: 43
ttacgcaatc ac                                                      12

<210> SEQ ID NO 44
<211> LENGTH: 20
<212> TYPE: DNA
<213> ORGANISM: Artificial Sequence
<220> FEATURE:
<223> OTHER INFORMATION: synthetic construct

<400> SEQUENCE: 44
acggaggcta agcgtcgcaa                                              20

<210> SEQ ID NO 45
<211> LENGTH: 12
<212> TYPE: DNA
<213> ORGANISM: Artificial Sequence
<220> FEATURE:
<223> OTHER INFORMATION: synthetic construct

<400> SEQUENCE: 45
aagtcttgct ag                                                      12

<210> SEQ ID NO 46
<211> LENGTH: 20
<212> TYPE: DNA
<213> ORGANISM: Artificial Sequence
<220> FEATURE:
<223> OTHER INFORMATION: synthetic construct

<400> SEQUENCE: 46
tactaacgcc gctcctacag                                              20
```

<210> SEQ ID NO 47
<211> LENGTH: 12
<212> TYPE: DNA
<213> ORGANISM: Artificial Sequence
<220> FEATURE:
<223> OTHER INFORMATION: synthetic construct

<400> SEQUENCE: 47
ccccataaat ag                                                           12

<210> SEQ ID NO 48
<211> LENGTH: 20
<212> TYPE: DNA
<213> ORGANISM: Artificial Sequence
<220> FEATURE:
<223> OTHER INFORMATION: synthetic construct

<400> SEQUENCE: 48
tagacaaccg cggagaatgc                                                   20

<210> SEQ ID NO 49
<211> LENGTH: 12
<212> TYPE: DNA
<213> ORGANISM: Artificial Sequence
<220> FEATURE:
<223> OTHER INFORMATION: synthetic construct

<400> SEQUENCE: 49
agctattggt gc                                                           12

<210> SEQ ID NO 50
<211> LENGTH: 66
<212> TYPE: DNA
<213> ORGANISM: Artificial Sequence
<220> FEATURE:
<223> OTHER INFORMATION: oligonucleotide primer

<400> SEQUENCE: 50
aatgatacgg cgaccaccga gatctacacg cctgtccgcg gaagcagtgg tatcaacgca       60
gagtac                                                                  66

<210> SEQ ID NO 51
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 51
gtctcgtggg ctcggagatg tgtataagag acagagcaag ttaaaataag gctagtccg        59

<210> SEQ ID NO 52
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 52
aatgatacgg cgaccaccga                                                   20

<210> SEQ ID NO 53
<211> LENGTH: 59
<212> TYPE: DNA
<213> ORGANISM: Artificial Sequence

```
<220> FEATURE:
<223> OTHER INFORMATION: oligonucleotide primer

<400> SEQUENCE: 53
gtctcgtggg ctcggagatg tgtataagag acagagcaag ttaaaataag gctagtccg      59
```